(12) United States Patent
Steiner et al.

(10) Patent No.: US 9,522,892 B2
(45) Date of Patent: Dec. 20, 2016

(54) ANTICOAGULANT REVERSAL AGENTS

(71) Applicant: PEROSPHERE INC., Mount Kisco, NY (US)

(72) Inventors: Solomon S. Steiner, Mount Kisco, NY (US); Bryan E. Laulicht, Cambridge, MA (US); Sasha H. Bakhru, Providence, RI (US); Edith Mathiowitz, Brookline, MA (US)

(73) Assignee: PEROSPHERE INC., Danbury, CT (US)

( * ) Notice: Subject to any disclaimer, the term of this patent is extended or adjusted under 35 U.S.C. 154(b) by 504 days.

(21) Appl. No.: 13/688,442

(22) Filed: Nov. 29, 2012

(65) Prior Publication Data
US 2013/0137702 A1    May 30, 2013

Related U.S. Application Data

(60) Provisional application No. 61/564,559, filed on Nov. 29, 2011, provisional application No. 61/614,292, filed on Mar. 22, 2012, provisional application No. 61/641,698, filed on May 2, 2012, provisional application No. 61/666,291, filed on Jun. 29, 2012.

(51) Int. Cl.
| | |
|---|---|
| *A61K 31/497* | (2006.01) |
| *C07D 241/04* | (2006.01) |
| *A61K 31/122* | (2006.01) |
| *A61K 31/4965* | (2006.01) |
| *C07D 295/13* | (2006.01) |

(52) U.S. Cl.
CPC ........... *C07D 241/04* (2013.01); *A61K 31/122* (2013.01); *A61K 31/4965* (2013.01); *C07D 295/13* (2013.01)

(58) Field of Classification Search
CPC ... C07D 241/04; C07D 295/13; A61K 31/122; A61K 31/31; A61K 31/4965
USPC ..................... 514/252.12; 544/400
See application file for complete search history.

(56) References Cited

U.S. PATENT DOCUMENTS

| 3,678,157 A * | 7/1972 | Kalopissis ............. A61K 8/416 424/47 |
| 6,713,622 B1 | 3/2004 | Graham et al. |
| 2003/0139405 A1 | 7/2003 | South et al. |

FOREIGN PATENT DOCUMENTS

| JP | 2004-21267 A | 1/2004 |
| JP | 2005-529860 A | 10/2005 |
| WO | 98/16547 A1 | 4/1998 |
| WO | 00/69833 A1 | 11/2000 |
| WO | 00/76982 A1 | 12/2000 |
| WO | 01/79155 A2 | 10/2001 |
| WO | WO03082809 A1 * | 10/2003 |
| WO | 2011/077158 A1 | 6/2011 |
| WO | 2011/089183 A2 | 7/2011 |
| WO | 2012/130834 A1 | 10/2012 |

OTHER PUBLICATIONS

Roch-Arveiller et al ( Eur. J. Clin. Chem. Clin. Biochem., 1997, 35(10), 743-748).*
Opposition filed by Generic Pharmaceutical Association (Asociació de Genéricos Farmacéuticos—AGEFAR) against Costa Rican Application No. 2014-0310, dated Dec. 5, 2014 (8 pages).
Sigma-Aldrich Chemie GmbH Catalogue, pp. 497, 502, 1305 (1996).
Bischoff, F., "Preparation of some substituted guanidines", J. Biol. Chem.,vol. 80, pp. 345-355 (1928).
Mull, R.P., et al., "Guanidines with antihypertensive Activity, II", J. Med. Pharm. Chem., vol. 5, pp. 944-949 (1962).
Hammam, A.H., "Heterocyclic quinones VIII. Synthesis and spectra of new carbazoloquinone derivatives of naturally occurring amino acids", J. Appl. Chem. Biotechnol., vol. 26, pp. 667-682 (1976).
Kitamura, S., et al., "Potent Dibasic GPIIb/IIIa Antagonists with Reduced Prolongation of Bleeding Time: Synthesis and Pharmacological Evaluation of 2-Oxopiperazine Derivatives", J. Med. Chem., vol. 44, No. 15, pp. 2438-2450 (2001).
Crowther, M., et al., "Bleeding Risk and the Management of Bleeding Complications in Patients Undergoing Anticoagulant Therapy: Focus on New Anticoagulant Agents", Blood, vol. 111, No. 10, pp. 4871-4879 (2008).
Written Opinion of the International Searching Authority issued in PCT/US2012/066938, dated Mar. 7, 2013 (7 pages).
International Search Report issued in PCT/US2012/066938, dated Mar. 7, 2013 (6 pages).
Office Action issued in corresponding Colombian Application No. 14 137450 3, dated May 7, 2015 (7 pages).
Search Report and Written Opinion issued in corresponding Singapore Application No. 11201402713W, dated May 13, 2015 (20 pages).
Office Action issued in corresponding Chinese Application No. 201280060950.2, dated May 13, 2015 (8 pages).
Stonard, J. et al., 1994 Microbial Secondary Metabolites as a Source of Agrochemicals, in Natural and Engineered Pest Management Agents, edited by Paul Hedin et al. Washington D.C., American Chemical Society: 25-36.
CAS Registry 500340-65-8 Mar. 24, 2003.
New Zealand Examination Report for NZ625337 dated Sep. 7, 2016.

(Continued)

*Primary Examiner* — Jason Sims
*Assistant Examiner* — Ibrahim D Bori
(74) *Attorney, Agent, or Firm* — Fitzpatrick, Cella, Harper & Scinto

(57) ABSTRACT

Novel anticoagulant reversal compounds are disclosed, as well as methods of making the compounds, pharmaceutical compositions including the compounds, methods of using the compounds to reverse the anticoagulant effects of coagulation inhibitors, and diagnostic assays comprising the compounds.

18 Claims, 12 Drawing Sheets

(56) References Cited

OTHER PUBLICATIONS

Japanese Office Action for JP20140544857 dated Aug. 8, 2016 and English Language Translation.

* cited by examiner

* Indicates below the limit of detection

Dabigatran

ANTICOAGULANT REVERSAL AGENTS

This application claims the benefit of priority from U.S. Provisional Patent Application No. 61/564,559, which was filed on Nov. 29, 2011, U.S. Provisional Patent Application No. 61/614,292, which was filed on Mar. 22, 2012, U.S. Provisional Patent Application No. 61/641,698, which was filed on May 2, 2012, and U.S. Provisional Patent Application No. 61/666,291, which was filed on Jun. 29, 2012, the contents of which are incorporated herein in their entirety.

FIELD OF THE INVENTION

The present invention discloses compounds that completely or partially reverse anticoagulant effects of coagulation inhibitors, such as unfractionated heparin ("UFH"), low molecular weight heparin ("LMWH"), fondaparinux, and other antithrombin binding anticoagulants, as well as direct Xa and IIa inhibitors.

BACKGROUND OF THE INVENTION

The coagulation cascade is a normal physiological process which aims at preventing significant blood loss or hemorrhage following vascular injury. There are times, however, when a blood clot (thrombus) will form when it is not needed. For instance, some high risk conditions such as acute medical illness, prolonged immobilization, surgery, or cancer can increase the risk of developing a blood clot which can potentially lead to significant consequences such as atherosclerotic cardiovascular disease and/or abnormal cardiac rhythms.

The coagulation cascade consists of a series of steps in which a protease cleaves and subsequently activates the next protease in the sequence. Each protease can activate several molecules of the next protease in the series, amplifying this biological cascade. The final result of these reactions is to convert fibrinogen, a soluble protein, to insoluble threads of fibrin. Together with platelets, the fibrin threads form a stable blood clot.

Antithrombin (AT), a serine protease inhibitor, is the major plasma inhibitor of coagulation proteases. AT blocks the coagulation cascade by, e.g., inhibiting thrombin (factor IIa) and activated factor X (factor Xa). Heparin (unfractionated heparin) and low molecular weight heparins (LMWHs; fractionated heparin) inhibit the coagulation process through binding to AT via a pentasaccharide sequence. This binding leads to a conformational change of AT, which accelerates its inhibition of factors IIa, Xa, and other proteases involved in blood clotting. Once dissociated, heparin and LMWH are free to bind to another antithrombin molecule and subsequently inhibit more thrombin and factor Xa.

Unfractionated heparin is a mixture of glycosaminoglycans (GAGs) discovered in the liver of dogs to have anticoagulant properties in 1916 by McLean and Howell at Johns Hopkins University. In addition to anti-coagulation, unfractionated heparin has been found to have other properties including anti-inflammation and angiogenesis. LMWHs are heparins consisting of short chains of polysaccharide, generally having molecular weight of less than 8000 Da. LMWH and heparin are both used to prevent blood from clotting inside the body, but are used in different situations in the clinic.

Heparin is available as a liquid solution administered parenterally. LMWH, such as enoxaparin, is a low molecular weight fraction of heparin. It is also available as a liquid injectable solution. The currently available brands of LMWH approved by FDA in the United States are LOVENOX® (generic name, enoxaparin) and FRAGMIN® (generic name, dalteparin).

Low molecular weight or fractionated heparin has greater specificity for blood factor Xa and factor IIa activity than unfractionated heparin. Additionally, LMWH has a more reproducible effect on activated partial thromboplastin time (aPTT), a measure of coagulation time. LWMH has a lower incidence of Heparin Induced Thrombocytopenia (HIT). Because LMWH has more predictable efficacy and a lower incidence of adverse effects such as HIT, patients can inject LMWH themselves at home, although it is also often used in the hospital. For these reasons, LMWHs have become the market-leading anticoagulant.

Protamine, a positively charged molecule, can be used to reverse anti-coagulation resulting from administration of highly negatively charged unfractionated heparin or low molecular weight heparin (LMWH). Protamine is a natural product that has been associated with supply problems, which highlights a need for additional, ideally synthetic, reversal agent options. The anti-coagulant activity of LMWH can be partially, but not fully, reversed by intravenous administration of protamine. The reason for the reduced anticoagulation reversal activity of protamine in the case of LMWH is believed to be due to a lesser binding affinity for the LMWH fraction in the blood than unfractionated heparin. Protamine must be administered slowly, due to hypotensive effects and concerns regarding anaphylaxis.

Recently, additional anticoagulant agents have begun to gain regulatory approval. Examples of such anticoagulants include dabigatran or PRADAXA®, argatroban or ARGATROBAN®, rivaroxaban or XARELTO®, apixaban or ELIQUIS®, edoxaban or LIXIANA®, and fondaparinux or ARIXTRA®. These anticoagulants inhibit either factor IIa or factor Xa from propagating coagulation.

Anticoagulants such as dabigatran, fondaparinux, rivaroxaban and apixaban have no approved reversal agent. The current state of the art for dabigatran or PRADAXA® reversal is to employ activated charcoal to attempt to remove dabigatran from the blood and to use blood transfusions. Other than Eerenberg et al. *Circulation*. 2011 Oct. 4; 124 (14):1573-9. Epub 2011 Sep. 6, which reports that in a small clinical trial, prothrombin complex concentrate was able to reverse dabigatran, but not rivaroxaban, there is no data or clinically available antidote for reversing any of these coagulation Factor IIa or Xa inhibitors. Therefore, when patients are anti-coagulated with these agents, adverse effects associated with overdosing, particularly significant or fatal bleeds, are much more dangerous than the side effects associated with administration of unfractionated heparin. The lack of reversal agent therefore limits the use of these drugs.

For these reasons, there is a longstanding, strong, unmet clinical need for new anti-coagulation reversal agents.

SUMMARY OF THE INVENTION

Inhibitors of heparin, heparin fragments, fondaparinux and other factor Xa or factor IIa inhibitors has been developed. The general structure of the anti-coagulant reversal agents of interest is: R—Z—R', where R and R' are positively charged agents at physiologic pH and can be the same or different molecules and Z is a hydrophobic cyclic or fused ring compound. More specifically, the inhibitor is represented by a compound of formula I or a pharmaceutically acceptable salt thereof:

Y-M-X-L-A-L'-X'-M'-Y'  (I)

wherein:

A is a substituted or unsubstituted aromatic or non-aromatic, carbocyclic or heterocyclic ring or a linear moiety;

L and L' are the same or different and are linkers;

X and X' are the same or different and are absent or are a functional group that attaches the linker L to M and the linker L' to M', respectively;

M and M' are the same or different and are absent or is a linker that attaches X to Y and X' to Y', respectively; and Y and Y' are the same or different and are a moiety containing one or more cationic atoms or groups or one or more groups that become cationic under physiological conditions.

The compounds can be symmetrical or asymmetrical; that is, one or more of L, L', X, X', M, M', Y, or Y' can be the same or different. The compounds can be chiral (i.e., contain one or more chiral centers) or achiral.

In some embodiments, A is a heterocyclic moiety. In other embodiments, A is a heterocyclic moiety and L and L' are a substituted or unsubstituted alkylene chain. In still other embodiments, A is a heterocyclic moiety, L and L' are a substituted or unsubstituted alkylene chain, and X and X' are —NH—C(=O)—. In still other embodiments, A is a heterocyclic moiety, L and L' are a substituted or unsubstituted alkylene chain, X and X' are —NH—C(=O)—, and M and M' are a substituted alkylene chain. In still other embodiments, A is a heterocyclic moiety, L and L' are a substituted or unsubstituted alkylene chain, X is —NH—C(=O)—, M and M' are a substituted alkylene chain, and Y and Y' are a guanidine moiety. In particular embodiments, A is a 1, 4 or 2,5 disubstituted piperazine ring.

In another embodiment of the invention the inhibitor is a compound represented by the formula II or a pharmaceutically acceptable salt thereof:

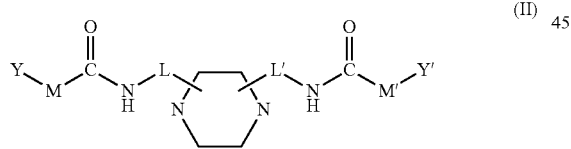

(II)

wherein each of L, L', M, M', Y and Y' are as described herein.

In another embodiment of the invention the inhibitor is a compound represented by the formula III or a pharmaceutically acceptable salt thereof:

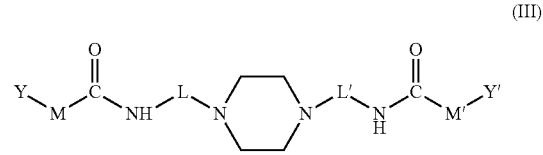

(III)

wherein L, L', M, M', Y and Y' are as described herein.

In yet another embodiment of the invention the inhibitor is a compound represented by the formula (IV) or pharmaceutically acceptable salt thereof:

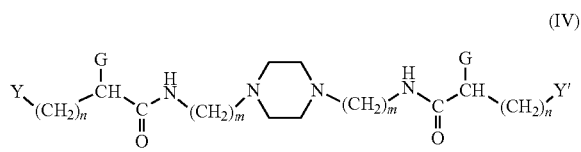

(IV)

wherein Y and Y' are as described herein and n is 3 to 5, m is 3 to 6 and G is selected from —NH$_2$ and OH. Most preferably, G is amino.

Yet another embodiment of the invention the inhibitor is a compound represented by any of formula II, III or IV and Y and Y' are independently selected from the group consisting of

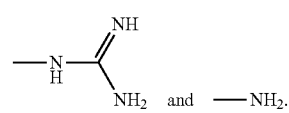

and —NH$_2$.

Most preferably G is —NH$_2$ and Y and Y' are

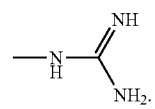

In the preferred embodiment, the compound is di-arginine piperazine (DAP), depicted in formula V, or a related compound, depicted in formula VI, or pharmaceutically acceptable salts of either compound:

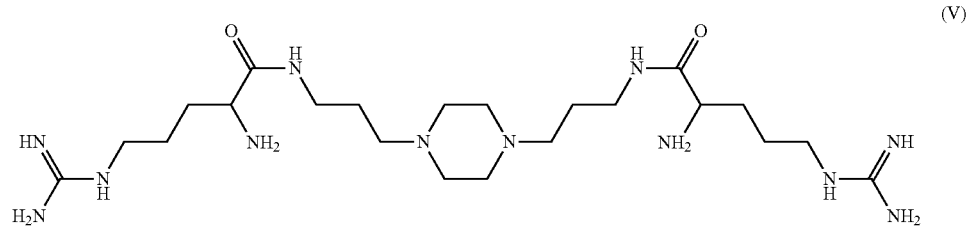

(V)

2-Amino-5-guanidino-pentanoic acid (3-{4-[3-(2-amino-5-guanidino-pentanoylamino)-propyl]-piperazin-1-yl}-propyl)-amide; or

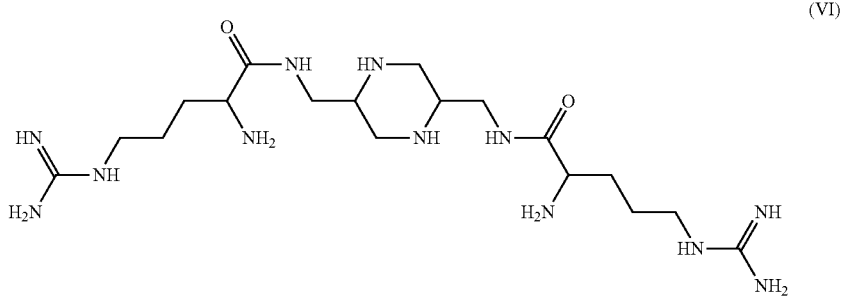 [SMILES: N=C(N)NCCCC(N)C(=O)NCC1CNC(CNC(=O)C(N)CCCNC(=N)N)CN1]

(VI)

2-Amino-5-guanidino-pentanoic acid {5-[(2-amino-5-guanidino-pentanoylamino)-methyl]-piperazin-2-ylmethyl}-amide.

In a specific embodiment, the compound of formula V is a stereoisomer as depicted in formula VII:

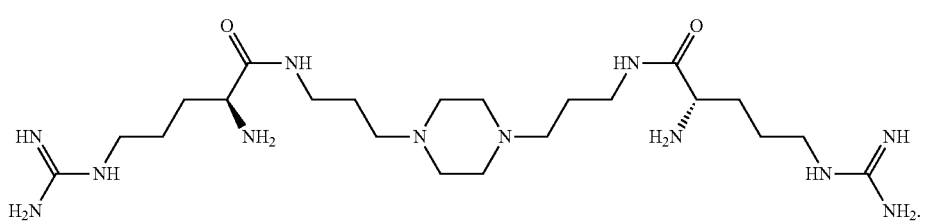

(VII)

In another specific embodiment, the compound of formula VI is a stereoisomer as depicted in formula VIII:

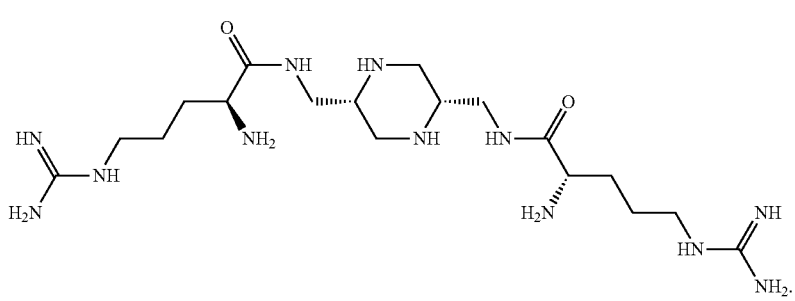

(VIII)

The compounds of the invention can be administered in a pharmaceutical composition as an aqueous solution as a bolus and/or intravenous infusion, subcutaneous injection, or orally. In the preferred embodiment, the compounds are administered by injection (intravenous, intramuscular or subcutaneous) in a carrier such as distilled sterile water, saline, buffered saline, or another pharmaceutically acceptable excipient for injection. In some embodiments, the inhibitor may be administered orally, to a mucosal surface (nasal, pulmonary, vaginal, rectal or buccal) or by depot.

The compounds of the invention may be administered in pharmaceutical composition to the patient in need of reversal of heparin, LMWH or other thrombin inhibitor-mediated anticoagulation in an effective amount to restore normal coagulation and hemostasis. The pharmaceutical compositions including the compound of the inventions are suitable for hospital use or in non-emergency home reversal. It is administered to the patient in need of reversal of heparin, LMWH or other thrombin inhibitor mediated anticoagulation in an effective amount to restore coagulation. The compounds and pharmaceutical compositions described herein can also be used to reduce the activity of heparin-binding growth factors and/or for reversing completely or in part a combination of one or more Factor IIa and/or Factor Xa anticoagulant agents.

Thus, the compounds of the invention can be used in a method of completely or partially reversing an anticoagulant effect of a coagulation inhibitor. The compounds of the invention can also be used as a part of a diagnostic kit, e.g., a diagnostic kit for determining concentration of an anticoagulant in the blood.

Examples demonstrate that DAP directly bound rivaroxaban, apixaban, unfractionated heparin, fondaparinux, and LMWH, reversing anticoagulant activity. DAP reversed oral rivaroxaban and subcutaneous LMWH anticoagulation in vivo as measured by aPTT and subcutaneous fondaparinux as measured by Xa activity in rats. DAP reversal, confirmed by statistically significant reduction in blood loss in tail rat transection assay, was shown for apixaban, dabigatran, edoxaban, and rivaroxaban. DAP completely reversed apixaban and rivaroxaban at a dose mass ratio of about 10:1 DAP:anticoagulant in human blood ex vivo as measured using an anti-Xa kit. DAP exhibited a dose-dependent reversal of apixaban and rivaroxaban in human blood ex vivo. Rivaroxaban reversal in freshly drawn human whole blood was confirmed by aPTT measurements ex vivo. DAP did not bind argatroban concentrations up to 1:1000 in vitro. DAP reversed oral dabigatran in vivo in rats as measured by aPTT. Argatroban dosed rats remained anticoagulated after a 200×IV dose of DAP, showing that DAP is safe and that the reversal interaction is specific for the heparins and new oral anticoagulants. In summary, the examples demonstrate complexation of DAP to heparin and LMWH and that DAP serves as an excellent reversal agent for heparin, heparin-like compounds and other thrombin inhibitors including dabigatran, approved low molecular weight heparins, as well as rivaroxaban (XARELTO®), fondaparinux (ARIX-TRA®), edoxaban (LIXIANA®), and apixaban (EL-IQUIS®), as tested in in vitro assays with human blood, anti-Xa and aPTT tests and/or in vivo in a rat tail transection assay.

DETAILED DESCRIPTION OF THE INVENTION

I. Anticoagulant Reversal Agents

Figure 1:
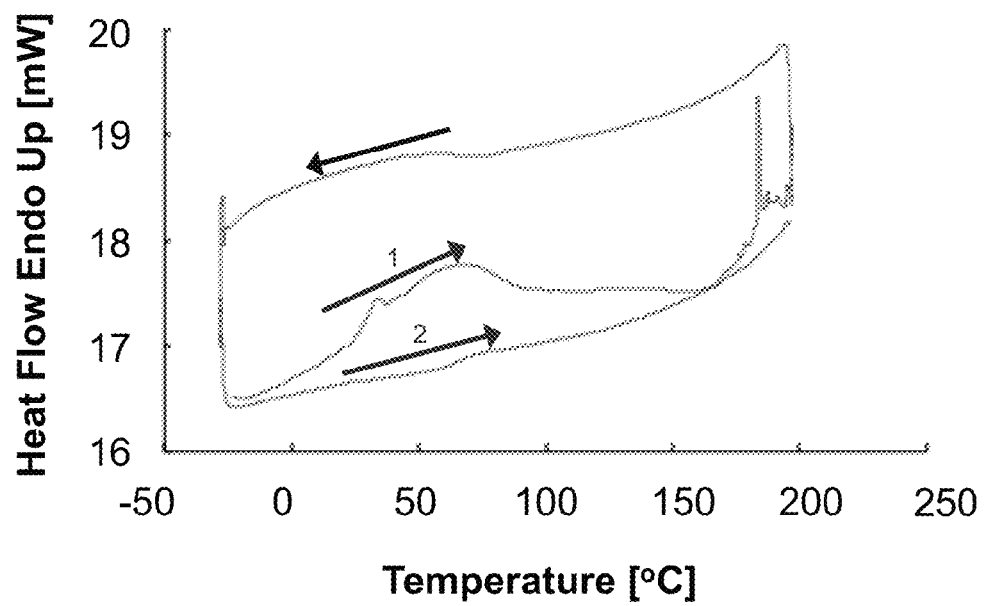
FIG. 1 is a graph of heat flow versus temperature as measured by differential scanning calorimetry (DCS) in which DAP is heated from −20° C. to 200° C. ("1" or "first heat"), cooled to −20° C., and heated back to 200° C. ("2" or "second heat").

Novel anticoagulant reversal agents are disclosed. The compounds of the invention include compounds described herein, as well as the pharmaceutically acceptable salts thereof.

Inhibitors of heparin, heparin fragments, fondaparinux and factor Xa or factor IIa inhibitors (e.g., oral factor Xa or factor IIa inhibitors) have been developed. The general structure of the anti-coagulant reversal agents of interest is: R—Z—R', where R and R' are positively charged agents at physiologic pH and can be the same or different molecules and Z is a hydrophobic cyclic or fused ring compound.

More specifically, the inhibitor is a compound of the formula (I) or pharmaceutically acceptable salt thereof:

Y-M-X-L-A-L'-X'-M'-Y'     (I)

wherein:

A is a substituted or unsubstituted aromatic or non-aromatic, carbocyclic or heterocyclic ring or a linear moiety;

L and L' are the same or different and are linkers;

X and X' are the same or different and are absent or are a functional group that attaches the linker L to M and the linker L' to M', respectively;

M and M' are the same or different and are absent or is a linker that attaches X to Y and X' to Y', respectively; and Y and Y' are the same or different and are a moiety containing one or more cationic atoms or groups or one or more groups that become cationic under physiological conditions.

The compounds can be symmetrical or asymmetrical; that is, one or more of L, L', X, X', M, M', Y, or Y' can be the same or different. The compounds can be chiral (i.e., contain one or more chiral centers) or achiral.

In some embodiments, A is a heterocyclic moiety. In other embodiments, A is a heterocyclic moiety and L and L' are a substituted or unsubstituted alkylene chain. In still other embodiments, A is a heterocyclic moiety, L and L' are a substituted or unsubstituted alkylene chain, and X and X' are —NH—C(=O)—. In still other embodiments, A is a heterocyclic moiety, L and L' are a substituted or unsubstituted alkylene chain, X and X' are —NH—C(=O)—, and M and M' are a substituted alkylene chain. As used herein, alkylene chain is a divalent alkelene moiety that is $C_1$ to $C_{10}$, preferably $C_3$ to $C_6$ in length, and which may be substituted or unsubstituted. Exemplary substituents include alkyl, hydroxyl, hydroxyl alkyl, amino, amino alkyl, alkoxy, alkyl alkoxy. As used herein, the term alkyl is $C_1$ to $C_{10}$, preferably $C_1$-$C_6$ straight chain or branched hydrocarbon. In still other embodiments, A is a heterocyclic moiety, L and L' are a substituted or unsubstituted alkylene chain, X is —NH—C(=O)—, M and M' are a substituted alkylene chain, and Y and Y' are a guanidine moiety.

In some embodiments, A is a non-aromatic, heterocyclic ring, such as piperazine or diketopiperazine. In other embodiments, A is a linear moiety, such as a linear diamine or other linear moiety containing reactive functional groups that can form a bond to X and X', when present, or Y and Y'. In some embodiments, the linkers L and L' are attached to the heteroatoms in the ring A, such as the two nitrogen atoms in piperazine. In other embodiments, the linker L and L' are attached to atoms other than the heteroatoms in the ring, such as carbon. In particular embodiments, A is a 1,4 or 2,5 disubstituted piperazine ring. In some embodiments, L and L' and/or M and M' are a substituted or unsubstituted alkylene chains, such as —$(CH_2)_n$—, where n is an integer from 1-10, preferably from 1-6, e.g., 1-3. In particular embodiments, n is 3. In some embodiments, L and/or M are absent.

X and X' are a functional group that attaches the linkers L and L' to Y and Y'. Exemplary functional groups include, but are not limited to, esters, amides, carbonates, and ketones. In particular embodiments, X and X' are a functional group that is resistant to simple hydrolysis, such as an amide group.

Y and Y' are a moiety that contains one or more atoms or groups that are cationic or will be cationic under physiological conditions. Examples include amine and guanidine moieties as well as phosphorous containing moieties, such as alkyltriphenylphosphonium, tetraphenylphosphonium, tetraphenylarsonium, tribenzyl ammonium, and phosphonium moieties. Additional cationic moieties include cationic oligomers and polymers, such as oligo- or polylysine, oligo- or polyarginine, N-alkylated polyethylene imine, and the like. Other cationic moieties include delocalized lipophilic cations containing one to three carbimino, sulfimino, or phosphinimino units as described in Kolomeitsev et al., *Tet. Let.*, Vol. 44, No. 33, 5795-5798 (2003).

In some embodiments, the compound is a piperazine derivative, wherein the amino acid side chains contain one or more positively charged atoms or atoms that will be positively charged under physiological conditions. Examples include diarginine piperazine. Other amino acids that are positively charged or will be positively charged under physiological conditions can be substituted for arginine.

"Aromatic", as used herein, refers to 5-12-membered, preferably 5-, 6- and 7-membered aromatic, heterocyclic, fused aromatic, fused heterocyclic, biaromatic, or biheterocyclic ring systems, optionally substituted. Broadly defined, "Ar", as used herein, includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "Ar" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(R) wherein R is absent or is H, O, ($C_{1-4}$)alkyl, phenyl or benzyl, and optionally containing 1-3 double bonds and optionally substituted with one or more substituents. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

In another embodiment of the invention the inhibitor is a compound represented by the formula II or a pharmaceutically acceptable salt thereof:

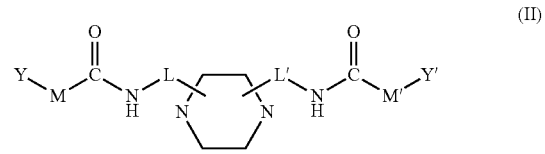

(II)

wherein each of L, L', M, M', Y and Y' are as previously described.

In another embodiment of the invention the inhibitor is a compound represented by the formula III or a pharmaceutically acceptable salt thereof:

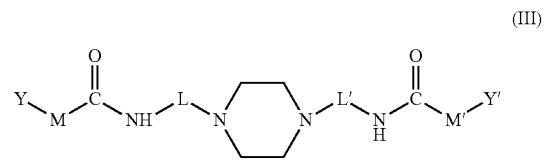

(III)

wherein L, L', M, M', Y and Y' are as previously described.

In yet another embodiment of the invention the inhibitor is a compound represented by the formula (IV) or pharmaceutically acceptable salt thereof:

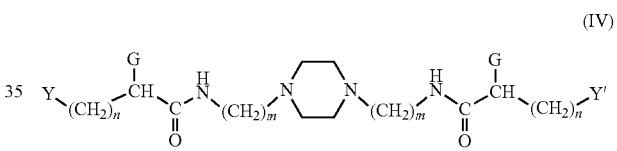

(IV)

wherein Y and Y' are as previously described and n is 3 to 5, m is 3 to 6 and G is selected from —$NH_2$ and OH. Most preferably, G is amino.

Yet another embodiment of the invention the inhibitor is a compound represented by any of formula II, III or IV and Y and Y' are independently selected from the group consisting of

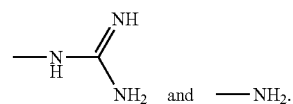

and —$NH_2$.

Most preferably G is —$NH_2$ and Y and Y' are

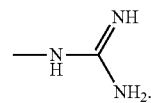

Thus, in one embodiment, the compound of the invention is di-arginine piperazine ("DAP"), such as the compound of formula V, or a related compound of formula VI, or pharmaceutically acceptable salts of either compound:

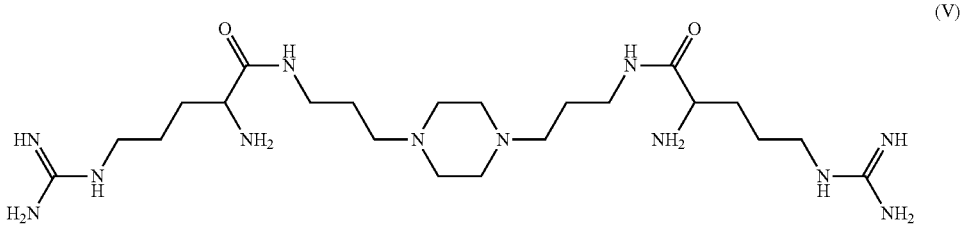

2-Amino-5-guanidino-pentanoic acid (3-{4-[3-(2-amino-5-guanidino-pentanoylamino)-propyl]-piperazin-1-yl}-propyl)-amide; or

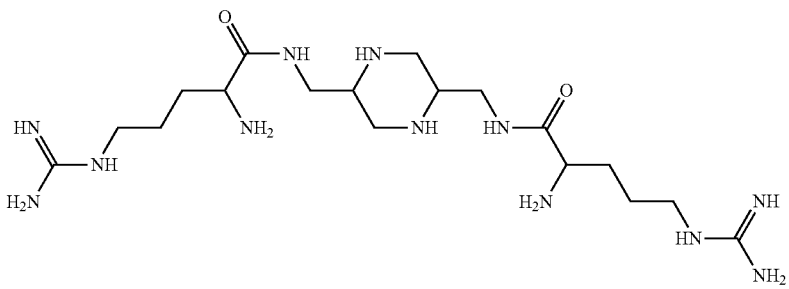

2-Amino-5-guanidino-pentanoic acid {5-[(2-amino-5-guanidino-pentanoylamino)-methyl]-piperazin-2-ylmethyl}-amide.

In a specific embodiment, the compound of formula V is a stereoisomer as depicted in formula VII:

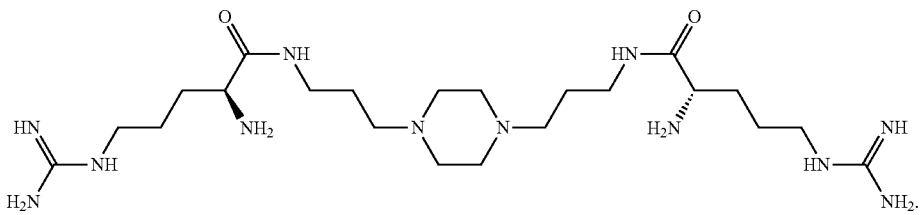

In another specific embodiment, the compound of formula VI is a stereoisomer as depicted in formula VIII:

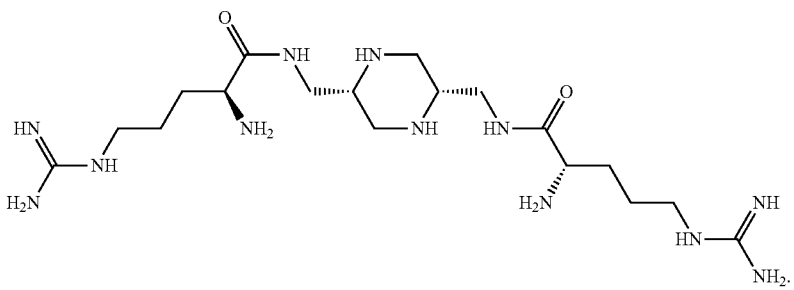

The phrase "pharmaceutically acceptable salt" of a compound as used herein means a salt that is pharmaceutically acceptable and that possesses the desired pharmacological activity of the parent compound. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Suitable base salts include, but are not limited to, aluminum, calcium, lithium, magnesium, potassium, sodium, zinc, and diethanolamine salts.

The compound of the invention inhibits activity of coagulation inhibitors. One proposed mechanism of action of the compound of the invention is through binding negatively charged molecules (e.g., fondaparinux, unfractionated heparin, LMWH, described herein). Other coagulation inhibitors (e.g., factor IIa and factor Xa inhibitors such as dabigatran, apixaban, edoxaban, and rivaroxaban, described herein) also possess negative charges; thus, the compound of the invention may inhibit these coagulation inhibitors through neutralization of their negatively charged moieties.

Another proposed mechanism of action of the compound of the invention is through weak physical interactions such as hydrogen bonding and hydrophobic interactions with the coagulation inhibitors. Oral Factor IIa and Xa inhibitors possess hydrophobic portions, which may cause hydrophobic association with the compound of the invention, e.g., DAP.

Thus, in some embodiments, the compounds of the invention contain at least one cyclic hydrophobic moiety, e.g., one or a combination of aliphatic or aromatic rings including fused rings. In other embodiments, the compounds of the invention contain at least one cyclic hydrophobic moiety and a least two positively charged or partially charged moieties at physiological pH.

In some embodiments of the invention, one or both arginines of the compounds of Formulas V and VI (or the compounds of Formulas VII and VIII) are substituted by one or more positively charged amino acids, their derivatives, or similarly charged compounds, e.g., lysine, histidine, ornithine. The arginines in the compounds of Formulas V and VI or positively charged amino acids substituted for such arginines can be naturally occurring amino acids (i.e., L-amino acids), their enantiomers (i.e., D-amino acids), or racemic or other mixtures thereof. "Enantiomers" refer to two stereoisomers of a compound which are non-superimposable minor images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes D and L or (+) and (−) are employed to designate the sign of rotation of plane-polarized light by the compound, with (−) or L meaning that the compound is levorotatory. A compound prefixed with (+) or D is dextrorotatory. For a given chemical structure, these stereoisomers are identical except that they are minor images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

In other embodiments of the invention, the compound of the invention contains at least one cyclic hydrophobic moiety, e.g., one or a combination of aliphatic and aromatic rings including fused rings. Compounds of interest contain at least one cyclic hydrophobic moiety and at least two positively charged or partially charged moieties at physiological pH.

Special consideration should be given to the design of peptide-based therapeutic agents, since such agents may cause unwanted and often severe immunological reactions once administered to a subject. The compound of the invention is designed to be of sufficiently low molecular weight to minimize immunogenicity issues. In one embodiment, in order to avoid activation of the immune response, the compound is designed such that its molecular weight is less than about 5000 daltons, such as less than or about 1000 daltons, e.g., about 500 daltons. In one embodiment, the molecular weight of the compound is about 512 daltons.

It is preferable that the compounds of the invention do not bind, or otherwise interfere with the function of the ERG, a potassium ion channel that contributes to the electrical conductivity of the heart. Inhibition of this potassium channel may lead to potentially fatal long QT syndrome, and some otherwise successful drug candidates have exhibited human ERG binding.

In addition, it is preferable that the compound of the invention does not inhibit or serve as substrates for membrane-bound cytochrome p450 (CYP) enzymes. CYPs are major enzymes involved in drug metabolism, and modulation of CYP activity may interfere with clearance and metabolism of other drugs administered to a subject, causing unwanted drug interactions.

Also preferably, the compounds of the invention do not exhibit significant plasma protein binding in vitro (e.g., albumin binding). Because the compounds of the invention are largely unbound to plasma proteins, they exhibit short activity half-lives minimizing the risk of accumulation-based overdose.

II. Synthesis of Anticoagulant Reversal Agents

The compounds and their pharmaceutically acceptable salts described herein are prepared using a variety of methods starting from commercially available compounds, known compounds, or compounds prepared by known methods. Exemplary synthetic routes to one of the compounds described herein (Compound of Formula V, di-arginine piperazine, "DAP") are included in the schemes below. The schemes below are also applicable to the DAP stereoisomer compound of Formula VII by selecting the appropriate stereoisomeric starting compounds. Other compounds of the invention may be synthesized following a similar synthetic scheme. It is understood by those skilled in the art that the order of steps shown herein may be changed to accommodate functionality in the target molecule. It is also understood by those skilled in the art that various protection and deprotection steps may be required for synthesis. The need for protection and deprotection, and the selection of appropriate protecting groups are found, for example, in Greene and Wuts, Protecting Groups in Organic Synthesis, Second Edition, John Wiley & Sons (1991), which is incorporated herein by reference in its entirety.

In some embodiments of the present invention, the protecting group is tertiary butyloxycarbonyl group (Boc). In other embodiments of the present invention, the protecting group is 2,2,4,6,7-Pentamethyldihydrobenzofuran-5-sulfonyl group (Pbf). In another embodiment, amino acid protecting group may be, but is not limited to, 2,2,5,7,8-pentamethyl-chroman-6-sulphonyl (PMC).

Protecting groups may be removed by a variety of routes. Removal of protecting group comprises, e.g., treating protected compound with trifluoroacetic acid (TFA), aqueous HCl, or heating in acetic acid. Because removal of protecting groups, e.g., removal of protecting groups under acidic conditions, can result in production of cationic species that can alkylate the functional groups on the peptide chain, scavengers may be added during the deprotection step to react with any of the free reactive species. Examples of scavengers include, but are not limited to, water, anisol derivatives and thiol derivatives. Thus, in one embodiment, removal of protecting groups comprises treating protected compound with TFA and a scavenger (e.g., TFA and water).

Various solvents, e.g., organic solvents, may be used in the steps of the synthesis. Appropriate solvents include, but are not limited to, dimethyl sulfoxide, dimethylformamide (DMF), tetrahydrofuran, methanol, ethanol, methylene chloride, toluene, and acetone. In some embodiments, the solvent is DMF.

Suitable acid binding agents may be used in the steps of the synthesis. These include, but are not limited to, organic bases, such as, for example, pyridine, triethylamine, triethanolamine, 1,8-diazabicyclo[5.4.0]undec-7-ene (DBU), and diisopropylethylamine (DIEA); and inorganic bases, such as, for example, sodium hydride, potassium carbonate, and sodium carbonates. In some embodiments, the acid binding agent is DIEA.

Synthesis may include peptide coupling reagents. Peptide coupling reagents may include, but are not limited to, 1-ethyl-3-(3-dimethylaminopropyl) carbodiimide (EDC), N-Hydroxybenzotriazole (HOBt), carbonyldiimidazole (CDI), dicyclohexylcarbodiimide (DCC), active N-hydroxysuccinamide (OSu) ester, O-Benzotriazole-N,N,N',N'-tetramethyl-uronium-hexafluoro-phosphate (HBTU), and combinations thereof. In one embodiment, the peptide coupling reagent is HBTU. In another embodiment, the peptide coupling reagent is EDC/HOBt. In yet another embodiment, the peptide coupling reagent is an active OSu ester.

Additionally, the synthesis may include a step in which a crude product is purified, e.g., by column chromatography. The desired products of each step or series of steps may be separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

In one scheme, the compound of Formula V (DAP)

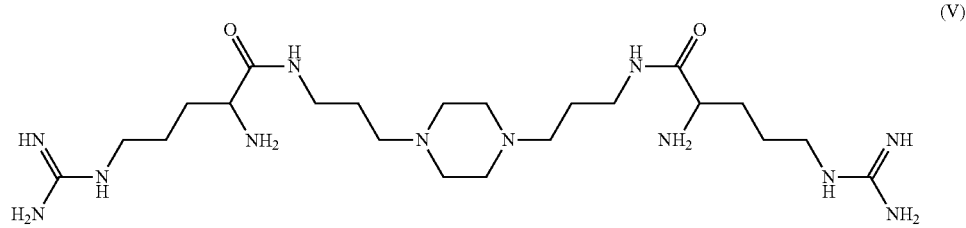 [SMILES: N=C(N)NCCCC(N)C(=O)NCCCN1CCN(CCCNC(=O)C(N)CCCNC(=N)N)CC1]

(V)

is synthesized by reacting excess equivalents (e.g., at least about two equivalents) of compound 1

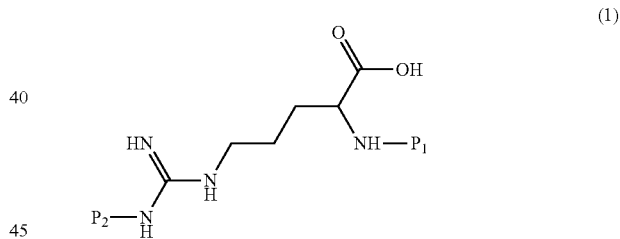

(1)

with one equivalent of compound 2

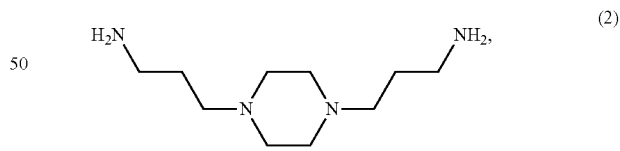

(2)

in the presence of a peptide coupling reagent, to obtain a compound 3

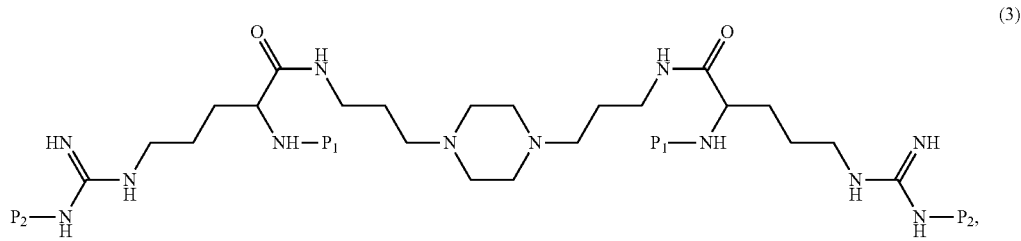

(3)

wherein P1 is a protecting group and P2 is a protecting group or is a hydrogen.

In one embodiment, the peptide coupling reagent is HBTU, EDC/HOBt, or an active OSu ester. In one embodiment, the protecting group P1 is Boc. In another embodiment, the protecting group P2 is Pbf. In a different embodiment, the protecting group P1 is Boc and P2 is a hydrogen.

Subsequently, 3 may be purified. This purification may involve various column chromatography methods known in the art.

Protecting groups of 3 may be removed by a variety of methods known in the art in order to obtain the compound of Formula V. Deprotection can be achieved by, e.g., removal of protecting groups using trifluoroacetic acid (TFA) and water, TFA and water or another scavenger, including, but not limited to aqueous HCl, or heating in acetic acid.

The compound may be further purified using a column chromatography method, such as ion exchange chromatography with salt buffers or preparative HPLC with trifluoroacetic acid or acetic acid as a buffer.

In a more specific scheme, the coupling involved reacting compound 1, wherein P1 was Boc and P2 was a hydrogen (depicted as Boc-Arg-OH.HCl below), with compound 2 as depicted below:

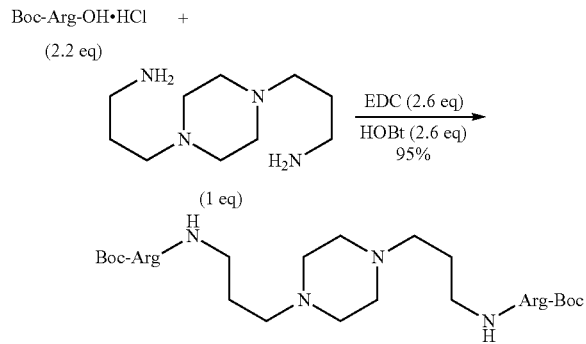

The resultant crude product was more than 95% pure by thin layer chromatography (TLC).

Subsequently, the deprotection step was carried out as depicted below:

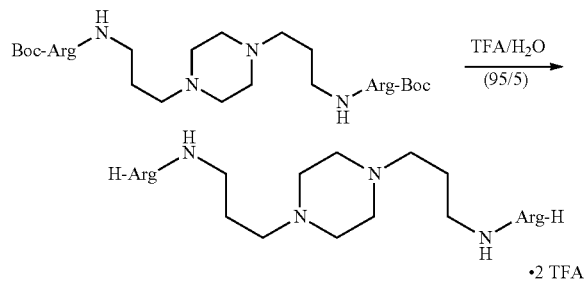

The deprotected product was purified by preparative HPLC using 1% acetic acid buffer. Product purity of ≥98% was observed. Residual TFA was removed by low quantity of DOWEX resin. The molecular weight of DAP (the compound of Formula V) is 512.4, and the compound synthesized according to the above scheme exhibited the following primary peak by mass spectroscopy: $[M+H]^+=513.4$.

III. Pharmaceutical Compositions

Pharmaceutical compositions comprising the compounds described herein are provided. Such a composition may contain, in addition to the compound of the invention, a pharmaceutically acceptable carrier or excipient. The term "pharmaceutically acceptable" means a nontoxic material that is compatible with the physical and chemical characteristics of the active ingredient and does not interfere with the effectiveness of the biological activity of the active. The compositions may contain various diluents, fillers, salts, buffers, stabilizers, solubilizers, and other materials well known in the art. The characteristics of the carrier will depend on the route of administration, and are generally well known in the art.

The pharmaceutical composition of the invention may be adapted for enteral administration-administration of the composition, wherein the composition is absorbed through the digestive tract, e.g., oral ingestion, rectal administration. In other embodiments, the pharmaceutical composition of the invention may be adapted for parenteral administration-administration of the composition, wherein the composition is introduced via a route other than digestive tract, e.g., intravenous, subcutaneous, cutaneous, nasal, pulmonary, vaginal, buccal route.

Suitable pharmaceutical compositions, e.g., compositions for oral administration, may be prepared as described in references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", $6^{th}$ Edition, Ansel et. al., (Media, Pa.: Williams and Wilkins, 1995), incorporated herein by reference, which provide information on carriers, materials (e.g., coating materials), equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), Zein, shellac, and polysaccharides. Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or non-ionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

Pharmaceutical compositions of the invention may be designed to provide delayed, sustained, pulsatile or other modified release.

If desired, the tablets, beads granules or particles may also contain minor amount of nontoxic auxiliary substances such as wetting or emulsifying agents, dyes, pH buffering agents, and preservatives.

Bioadhesive formulations may also be utilized to enhance uptake or modify release. Such formulations are known in the art. See, for example, US Patent Application No. 20060045865 by Jacob, incorporated herein by reference.

Pharmaceutical compositions adapted for delivery via nasal or pulmonary administration may also be useful. Aerosols for the delivery of therapeutic agents to the respiratory tract have been described, for example, Adjei, A. and Garren, J. *Pharm. Res.*, 7: 565-569 (1990); and Zanen, P. and Lamm, J.-W. J. *Int. J. Pharm.*, 114: 111-115 (1995). The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung. Gonda, I. "Aerosols for delivery of therapeutic and diagnostic agents to the respiratory tract," in *Critical Reviews in Therapeutic Drug Carrier Systems*, 6:273-313 (1990). The deep lung, or alveoli, is the primary target of inhaled therapeutic aerosols for systemic drug delivery.

Drugs administered by inhalation may come as liquid aerosol formulations.

For injectable compositions (e.g., intravenous compositions), the carrier is distilled sterile water, saline, buffered saline, or another pharmaceutically acceptable excipient for injection. Additives may include preservatives and acids or base to adjust pH, to alter solubility or uptake.

In one embodiment, wherein the pharmaceutical composition comprises the DAP compound of formula V (or its stereoisomer of formula VII) and the composition is adapted for parenteral administration in an injection, the compound is dissolved in water with appropriate tonicity and molality modifiers (such as phosphate buffered saline). DAP is water-soluble at greater than 100 mg/ml. In the one embodiment, DAP is adapted as a sterile solution for IV administration. In one aspect, the molality of the pharmaceutical composition in which DAP is adapted for IV administration is adjusted to 290 mOsm/L with sodium chloride, and the pH is adjusted to 7.4 with sodium hydroxide. Preferably the pharmaceutical composition is administered as an intravenous bolus by slow push.

IV. Methods of Use

The present invention provides a method of completely or partially reversing an anticoagulant effect of a coagulation inhibitor comprising administering to a subject in need thereof a therapeutically effective amount of a compound of the invention (e.g., a compound of formula I, II, III, IV, V, VI, VII, or VIII) or pharmaceutically acceptable salt thereof. The present invention also provides a method of promoting coagulation in a subject in need thereof, wherein the subject is receiving a coagulation inhibitor, comprising administering to the subject a therapeutically effective amount of a compound of the invention or a pharmaceutically acceptable salt thereof. In addition, the present invention provides a method of neutralizing or inhibiting a coagulation inhibitor comprising administering to a subject in need thereof a therapeutically effective amount of a compound of the invention or a pharmaceutically acceptable salt thereof.

In the present invention, coagulation inhibitor (also referred to herein as anticoagulant) is a molecule that inhibits coagulation process. Exemplary coagulation inhibitors include, but are not limited to, antithrombin activators (e.g., unfractionated heparin and LMWH), factor IIa inhibitors, and factor Xa inhibitors.

Heparin: Heparin is a naturally occurring mucopolysaccharide that acts in the body as an antithrombin co-factor to prevent intravascular clotting. The substance is produced by basophils and mast cells, which are found in large numbers in the connective tissue surrounding capillaries, particularly in the lungs and liver. In the form of sodium salt, heparin is used therapeutically as an anticoagulant.

Low Molecular Weight Heparin: Low Molecular Weight Heparin (LMWH) is made from heparin using various methods of depolymerization, including oxidative depolymerization with hydrogen peroxide, used in the manufacture of ardeparin (NORMIFLO®); deaminative cleavage with isoamyl nitrite, used in the manufacture of certoparin (SANDOPARIN®); alkaline beta-eliminative cleavage of the benzyl ester of heparin, used in the manufacture of enoxaparin (LOVENOX® and CLEXANE®); oxidative depolymerization with $Cu^{2+}$ and hydrogen peroxide, used in the manufacture of parnaparin (FLUXUM®); beta-eliminative cleavage by the heparinase enzyme, used in the manufacture of tinzaparin (INNOHEP® and LOGIPARIN®); deaminative cleavage with nitrous acid, used in the manufacture of dalteparin (FRAGMIN®), reviparin (CLIVARIN®) and nadroparin (FRAXIPARIN®), which results in the formation of an unnatural anhydromannose residue at the reducing terminal of the oligosaccharides produced. This can subsequently be converted to anhydromannitol using a suitable reducing agent. Both chemical and enzymatic beta-elimination result in the formation of an unnatural unsaturated uronate residue (UA) at the non-reducing terminal.

Summary of anticoagulant activities of several LMWHs is presented in Table 1.

TABLE 1

Molecular weight (MW) data and anticoagulant activities of currently available LMWH products.

| LMWH | Average molecular weight | Ratio anti-Xa/anti-IIa activity |
|---|---|---|
| BEMIPARIN | 3600 | 9.7 |
| CERTOPARIN | 5400 | 2.4 |
| DALTEPARIN | 6000 | 2.5 |
| ENOXAPARIN | 4500 | 3.9 |
| NADROPARIN | 4300 | 3.3 |
| PARNAPARIN | 5000 | 2.3 |
| REVIPARIN | 4400 | 4.2 |
| TINZAPARIN | 6500 | 1.6 |

Adapted from Gray E. et al., *Thromb Haemost*, 99: 807-818 (2008).

Clinically, LMWH (average molecular weight of about 4.5 kDa) differs from heparin (i.e., "unfractioned heparin"; average molecular weight of about 15 kDa) in a variety of ways: (a) LMWH requires less frequent subcutaneous dosing for postoperative prophylaxis of venous thromboembolism; (2) LMWH requires once or twice daily subcutaneous injection in patients treated for venous thromboembolism and unstable angina instead of intravenous infusion required with heparin; (3) LMWH requires no monitoring of the aPTT coagulation parameter; (4) LMWH poses a lower risk of bleeding; (5) long term use of LMWH poses a lower risk of osteoporosis; and (6) LMWH poses a lower risk of heparin-induced thrombocytopenia (a potential side effect of heparin administration). However, the anticoagulant effects of heparin are typically reversible with protamine sulfate, while protamine's effect on LMWH is limited. In addition, LMWH has less effect on thrombin (Factor IIa) activity compared to heparin, while both LMWH and heparin have a similar effect on Factor Xa activity.

Thrombin and Other Factor IIa or Xa Inhibitors: Examples of thrombin (Factor IIa) and factor Xa inhibitors include anticoagulants such as dabigatran (PRADAXA®), rivaroxaban (XARELTO®), apixaban (ELIQUIS®), edoxaban (LIXIANA®), fondaparinux (ARIXTRA®), and argatroban (ARGATROBAN®).

The chemical name for oral anticoagulant PRADAXA®, dabigatran etexilate mesylate, a direct thrombin inhibitor, is β-Alanine, N-[[2-[[[4-[[[(hexyloxy)carbonyl]amino]iminomethyl]phenyl]amino]methyl]-1-methyl-1H-benzimidazol-5-yl]carbonyl]-N-2-pyridinyl-, ethyl ester, methanesulfonate. Dabigatran and its acyl glucuronides are competitive, direct thrombin inhibitors. Because thrombin (Factor IIa, serine protease) enables the conversion of fibrinogen into fibrin during the coagulation cascade, its inhibition prevents the development of a thrombus.

Rivaroxaban, a factor Xa inhibitor, is the active ingredient in XARELTO®, and has the chemical name 5-Chloro-N-({(5S)-2-oxo-3-[4-(3-oxo-4-morpholinyl)phenyl]-1,3-oxazolidin-5-yl}methyl)-2-thiophenecarboxamide. Rivaroxaban is a pure (S)-enantiomer. XARELTO® is an orally bioavailable factor Xa inhibitor that selectively blocks the active site of factor Xa and does not require a cofactor (such as Anti-thrombin III) for activity.

Apixaban or ELIQUIS® is 1-(4-methoxyphenyl)-7-oxo-6-[4-(2-oxopiperidin-1-yl)phenyl]-4,5-dihydropyrazolo[5,4-c]pyridine-3-carboxamide. It is an orally administered direct factor Xa inhibitor approved in Europe and presently undergoing phase III trials in the U.S. for the prevention of venous thromboembolism.

Edoxaban or LIXIANA® is N'-(5-chloropyridin-2-yl)-N-[(1S,2R,4S)-4-(dimethylcarbamoyl)-2-[(5-methyl-6,7-dihydro-4H-[1,3]thiazolo[5,4-c]pyridine-2-carbonyl)amino] cyclohexyl]oxamide. Edoxaban is a direct factor Xa inhibitor, and it has been approved in Japan for use in preventing venous thromboembolism.

ARIXTRA® is fondaparinux sodium. It is a synthetic and specific inhibitor of activated Factor X (Xa). Fondaparinux sodium is methyl O-2-deoxy-6-O-sulfo-2-(sulfoamino)-α-D-glucopyranos yl-(1→4)-O-β-D-glucopyra-nuronosyl-(1→4)-O-2-deoxy-3,6-di-O-sulfo-2-(sulfoamino)-α-D-glucopyranosyl-(1→4)-O-2-O-sulfo-α-L-idopyranuronosyl-(1→4)-2-deoxy-6-O-sulfo-2-(sulfoamino)-α-D-glucopyranoside, decasodium salt. The molecular formula of fondaparinux sodium is $C_{31}H_{43}N_3Na_{10}O_{49}S_8$ and its molecular weight is 1728. The structural formula is provided below:

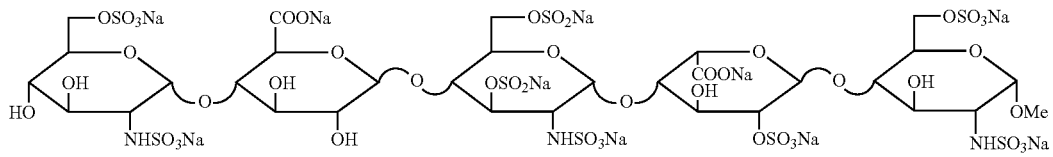

The antithrombotic activity of fondaparinux sodium is the result of antithrombin III (ATIII)-mediated selective inhibition of Factor Xa. By selectively binding to ATIII, fondaparinux sodium potentiates (about 300 times) the innate neutralization of Factor Xa by ATIII. Neutralization of Factor Xa interrupts the blood coagulation cascade and thus inhibits thrombin formation and thrombus development. Fondaparinux sodium does not inactivate thrombin (activated Factor II) and has no known effect on platelet function.

At the recommended dose, fondaparinux sodium does not affect fibrinolytic activity or bleeding time. The pharmacodynamics/pharmacokinetics of fondaparinux sodium are derived from fondaparinux plasma concentrations quantified via anti-factor Xa activity. Only fondaparinux can be used to calibrate the anti-Xa assay. (The international standards of heparin or LMWH are not appropriate for this use.) As a result, the activity of fondaparinux sodium is expressed as milligrams (mg) of the fondaparinux calibrator. The anti-Xa activity of the drug increases with increasing drug concentration, reaching maximum values in approximately three hours. Fondaparinux sodium administered by subcutaneous injection is rapidly and completely absorbed (absolute bioavailability is 100%). In patients undergoing treatment with fondaparinux sodium injection 2.5 mg, once daily, the peak steady-state plasma concentration is, on average, 0.39 to 0.50 mg/L and is reached approximately 3 hours post-dose. In these patients, the minimum steady-state plasma concentration is 0.14 to 0.19 mg/L. In patients with symptomatic deep vein thrombosis and pulmonary embolism undergoing treatment with fondaparinux sodium injection 5 mg (body weight <50 kg), 7.5 mg (body weight 50 to 100 kg), and 10 mg (body weight >100 kg) once daily, the body-weight-adjusted doses provide similar mean steady-state peaks and minimum plasma concentrations across all body weight categories. The mean peak steady-state plasma concentration is in the range of 1.20 to 1.26 mg/L. In these patients, the mean minimum steady-state plasma concentration is in the range of 0.46 to 0.62 mg/L.

ARGATROBAN® is a synthetic direct thrombin (Factor IIa) inhibitor, derived from L-arginine. The chemical name for ARGATROBAN® is 1-[5-[(aminoiminomethyl)amino]-1-oxo-2-[[(1,2,3,4-tetrahydro-3-methyl-8-quinolinyl)sulfonyl]amino]pentyl]-4-methyl-2-piperidinecarboxylic acid, monohydrate. The molecular formula of ARGATROBAN® is $C_{23}H_{36}N_6O_5S \cdot H_2O$. Its molecular weight is 526.66. ARGATROBAN® is a direct thrombin inhibitor that reversibly binds to the thrombin active site. ARGATROBAN® does not require the co-factor antithrombin III for antithrombotic activity. ARGATROBAN® is administered by injection, and it exerts its anticoagulant effects by inhibiting thrombin-catalyzed or thrombin-induced reactions, including fibrin formation; activation of coagulation factors V, VIII, and XIII; activation of protein C; and platelet aggregation.

An anticoagulant effect is any effect of a coagulation inhibitor (e.g., heparin, LMWH, Factor Xa inhibitor, Factor IIa inhibitor) that results from its blockage of the propagation of the coagulation cascades. Nonlimiting examples of anticoagulation effects include upregulation of antithrombin activity, decreased Factor Xa activity, decreased Factor IIa activity, increased blood loss, and any other conditions wherein the activity or concentrations of clotting factors are altered in such a way as to inhibit blood clot formation.

Activity of a coagulation inhibitor (i.e., its anticoagulant effects) may be measured by a variety of methods, including but not limited to a chromogenic anti-factor Xa activity assay, activated partial thromboplastin time assay, prothrombin time, bleeding assay (e.g., rat tail bleeding assay), thromboelastography, thrombin generation assay, dilute Russel's viper venom time, ecarin clotting time, kaolin clotting time, International Normalized Ratio (INR), fibrinogen testing (Clauss), thrombin time (TCT), mixing time, and euglobulin lysis time. These methods aid in determining various anticoagulation parameters, and are known to those skilled in the art. Thus, in some embodiments, anticoagulation can be monitored by one or a combination of the above listed assays.

The anti-factor Xa assay directly measures anti-factor Xa activity. The methodology behind an anti-factor Xa assay is that patient plasma is added to a known amount of excess factor Xa and excess antithrombin. If a factor Xa inhibitor is present in the patient plasma, it will reduce the enzymatic activity of factor Xa. The amount of residual factor Xa is inversely proportional to the amount of anti-Xa agent in the plasma. The amount of residual factor Xa is detected by adding a chromogenic substrate that mimics the natural substrate of factor Xa, making residual factor Xa cleave it, releasing a colored compound that can be detected by a spectrophotometer. Antithrombin deficiencies in the patient do not affect the assay, because excess amounts of antithrombin are provided in the reaction. Results are given in anticoagulant concentration in units/mL of antifactor Xa, such that high values indicate high levels of anticoagulation and low values indicate low levels of anticoagulation.

The activated partial thromboplastin time (aPTT) assay is an assay that measures how long it takes for the blood to clot. Blood samples are collected for direct measurement or in tubes with oxalate and citrate to arrest coagulation by calcium until the assay can be performed. In the assay, a phospholipid, an activator (silica, celite, kaolin, ellagic acid, etc.), and calcium are mixed into the plasma to induce coagulation. The assay measures the time until a thrombus (clot) forms.

Rat tail bleeding assay or rat tail transection assay is an assay that measures blood loss, e.g., blood loss after drug administration. In one embodiment, where the effect of the compound of the invention (e.g., DAP) is being tested, at the Tmax of the anticoagulant, DAP is administered intravenously. After 20 minutes, rat tails are transected approximately 1 mm from the tip, placed in room temperature saline, and blood is collected for 30 minutes and weighed.

Assays used to measure activity of coagulation inhibitors maybe used in the laboratory or in the clinic to measure reversal of an anticoagulant effect of a coagulation inhibitor, e.g., reversal of an anticoagulant effect of a coagulation inhibitor due to administration of a pharmaceutical composition comprising a compound of the invention. Thus, in one embodiment, the assays are utilized to measure complete or partial reversal of an anticoagulant effect of a coagulation inhibitor (such as heparin, LMWH, Factor IIa inhibitor, and Factor Xa inhibitor).

A complete reversal of an anticoagulant effect of a coagulation inhibitor occurs upon neutralization of the anticoagulant activity. In one embodiment, a complete reversal of an anticoagulant effect of a coagulation inhibitor, as measured by the anti-Xa activity assay, occurs when anticoagulant concentration is brought below the minimum effective concentration (MEC) for anticoagulation. MEC, as used herein, is a lowest amount of the drug (e.g., coagulation inhibitor) required for therapeutic effect. In another embodiment, a complete reversal of an anticoagulant effect of a coagulation inhibitor, as measured by the aPTT assay, occurs when the aPTT returns within about 10% of baseline. A baseline, as used herein, refers to aPTT in the absence of coagulation inhibitors.

In many cases, anticoagulation will still be desired, but to a lesser degree. Thus, a partial reversal of an anticoagulant effect of a coagulation inhibitor will be indicated. Partial reversal of an anticoagulant effect of a coagulation inhibitor, as measured by the anti-Xa activity assay, occurs when the anticoagulant concentration is brought below the anticoagulant concentration in the absence of an anticoagulation reversal agent (e.g., a compound of the invention), but remains above the MEC for anticoagulation. Thus, in some embodiments, partial reversal of an anticoagulation effect of coagulation inhibitors occurs when the concentration of anticoagulant is lower than about four times the MEC, preferably about twice the MEC, more preferably less than about twice the MEC (e.g., at about the MEC). Partial reversal of an anticoagulant effect of coagulation inhibitor, as measured by aPTT assay, occurs when aPPT is reduced below the measurement in the absence of an anticoagulation reversal agent (e.g., a compound of the invention) but above the baseline. Thus, in other embodiments, partial reversal of an anticoagulation effect of coagulation inhibitors occurs when the aPTT measurement is reduced below about four times the baseline, preferably about twice the baseline, more preferably less than about twice the baseline. Generally, the extent and duration of anticoagulation reversal is determined by the physician or veterinarian.

As used herein, "subject in need thereof" is a subject in need of either acute or planned reversal of anticoagulation, e.g., a subject suffering from anticoagulant overdose, a subject suffering from hemorrhage (e.g., trauma-induced hemorrhage or spontaneous hemorrhage in the GI tract or elsewhere), a subject requiring planned surgical intervention, a subject undergoing an invasive or non-invasive procedure requiring a biopsy, a subject undergoing a procedure wherein a procedural error may risk hemorrhage if the subject remains anticoagulated, a subject requiring spinal or epidural anesthesia. "Subject in need thereof" may be a patient in whom the presence of a direct factor inhibitor (Factor Xa, Factor IIa and/or antithrombin) is producing or is likely to produce bleeding effects. Thus, "subject in need thereof" may be a subject receiving anticoagulation therapy (e.g., subject receiving heparin, LMWH, Factor IIa inhibitor, or Factor Xa inhibitor) for, e.g., stroke prevention, cardiac surgical and diagnostic procedures, cardiac arrhythmias, deep vein thrombosis (DVT) prevention, pulmonary embolism, general prevention of the formation of pathologic blood clots.

"Subject in need thereof," as used herein, is an animal. "Subject in need thereof" includes, without limitation, a human, mouse, rat, guinea pig, dog, cat, horse, cow, pig, monkey, chimpanzee, baboon, or rhesus monkey. In one embodiment, "subject in need thereof" is a mammal. In another embodiment, "subject in need thereof" is a human.

As used herein, "therapeutically effective amount" refers to an amount of an anticoagulation reversal agent (e.g., a compound of the invention described herein), which is effective, upon single or multiple dose administration (e.g., bolus and/or maintenance doses) to a subject, in neutralizing or inhibiting (completely or partially reversing) an anticoagulant effect of a coagulation inhibitor or in promoting coagulation.

In one aspect, a therapeutically effective amount is a dose of an anticoagulation reversal agent that is between 0.01 and 10,000 times the anticoagulant dose by weight. In another aspect, the anticoagulation reversal agent is administered at a dose mass ratio of between about 1:1 and 1000:1 of the anticoagulation reversal agent to anticoagulant, e.g., 100:1 of the anticoagulation reversal agent to anticoagulant, such as 10:1 of anticoagulation reversal agent to anticoagulant. In one embodiment of the present method, a therapeutically effective amount of the anticoagulation reversal agent may be administered by subcutaneous, intramuscular, or intravenous route of administration. For example, it may be administered intravenously as a sterile solution. In another embodiment, a therapeutically effective amount of the anticoagulation reversal agent is administered by oral, nasal, or pulmonary route, or to a mucosal region (mouth, rectum, or vagina).

The therapeutically effective amount of the anticoagulation reversal agent (i.e., the compound of the invention) will typically range from about 0.001 mg/kg to about 1 g/kg of body weight per day; in another embodiment, from about 0.01 mg/kg to about 600 mg/kg body weight per day; in another embodiment, from about 0.01 mg/kg to about 250 mg/kg body weight per day; in another embodiment, from about 0.01 mg/kg to about 400 mg/kg body weight per day; in another embodiment, from about 0.01 mg/kg to about 200 mg/kg of body weight per day; in another embodiment, from about 0.01 mg/kg to about 100 mg/kg of body weight per day; in one embodiment, from about 0.01 mg/kg to about 25 mg/kg body weight per day; in another embodiment, from about 0.1 mg/kg to about 10 mg/kg body weight per day; in another embodiment, from about 0.001 mg/kg to about 100 mg/kg of body weight per day; in another embodiment, from about 0.001 mg/kg to about 10 mg/kg of body weight per day; and in another embodiment, from about 0.001 mg/kg to about 1 mg/kg of body weight per day. Standard coagulation assays (as those described herein) and other in vitro assays can be used to determine the therapeutically effective amount.

In some aspects of the invention, the compound of the invention may be co-administered with at least one additional therapeutic agent. In one embodiment, the at least one additional therapeutic agent may be vitamin K, which is typically used to correct clotting deficiencies induced by warfarin compounds.

The present invention also provides a diagnostic assay for determining the anticoagulant concentration in the blood. As shown in Example 13 below, DAP demonstrates a dose-responsive trend in reversing rivaroxaban ex vivo in human plasma using a 510 k-cleared anti-factor Xa chromogenic assay. Thus, the compound of the invention, e.g., DAP, can be used in a diagnostic assay to determine the concentration of an anticoagulant, e.g., a Factor Xa inhibitor, in the blood. In such an assay, the compound of the invention, e.g., DAP, can be used either in conjunction with the currently available kit reagents or as a direct binding substrate replacing synthetic factors present in currently available kits. In one embodiment, the diagnostic assay may comprise the compound of the invention (e.g., DAP) as a binding substrate, wherein the compound of the invention binds an anticoagulant in a blood sample, and the residual activity of the clotting factor (e.g., Factor Xa) is quantified to determine the concentration of the anticoagulant in the sample. In another embodiment, the diagnostic assay may comprise the compound of the invention (e.g., DAP) conjugated to magnetic microparticles, wherein the compound of the invention can bind an anticoagulant in a blood sample in order to either remove the anticoagulant from the sample or to concentrate it. The DAP-based chromogenic or point of care assay of the invention can aid in the determination of anticoagulant levels in subjects, which is currently a significant clinical unmet need since current diagnostics cannot determine blood concentrations of direct inhibitors with high accuracy.

Additionally, the present invention provides an assay, e.g., a chromogenic assay, to determine the concentration of the compound of the invention, e.g., DAP, required to reverse the anticoagulant present in the blood. In one embodiment, the assay uses DAP as a direct binding agent for various anticoagulants.

The invention also provides an assay, e.g., a chromogenic assay, to determine the amount of the compound of the invention, e.g., DAP, in the blood. Such assay may utilize predetermined concentrations of an anticoagulant.

The present invention also provides a diagnostic kit that incorporates a diagnostic assay described herein above. Thus, in one embodiment, the kit is used for determining the anticoagulant concentration in the blood. The kit may contain other components, packaging, instructions, reagents, and/or other material to aid in the determination of anticoagulant (e.g., Factor Xa inhibitor) or DAP concentration and to aid in the use of the kit. Additionally, the kit may be used to determine if there is a combination of warfarin and another anticoagulant as warfarin will be unaffected by the compound of the invention, while other anticoagulants will be reversed.

As demonstrated in the following examples, a compound of the invention (e.g., DAP) is capable of binding heparin, inactivating it in vivo. Thus, in addition to its effects on coagulation, a compound of the invention may also be used to deprive tissues of the biochemical activities of heparin. For example, other heparin-binding molecules have demonstrated the ability to reduce fibroblast growth factor (FGF), epidermal growth factor (EGF), vascular endothelial growth factor (VEGF), and other heparin binding growth factors. VEGF and FGF deprivation has been shown useful in anti-cancer therapy, making compounds of the invention possible candidates for the treatment of cancer. Therefore, in one aspect, the present invention provides a method for treating, preventing, or ameliorating a cancer in a subject, comprising administering to a subject a therapeutically effective amount of a compound of the invention or a pharmaceutically acceptable salt thereof.

As demonstrated in the examples, one compound of the invention, DAP, bound XARELTO®, ELIQUIS®, ARIXTRA® and LMWH in vitro as measured by dynamic light scattering (DLS). DAP reversed subcutaneously administered ARIXTRA® and LMWH in vivo. DAP reversed XARELTO®, ELIQUIS®, PRADAXA®, LIXIANA®, unfractionated heparin and bemiparin in vivo. DAP intravenously administered at 100 mg/kg, 250 mg/kg and 400 mg/kg doses in rats showed no adverse effect. DAP was orally bioavailable in rats. DAP exhibited no human ERG binding, did not inhibit or serve as a substrate of CYP enzymes, and did not appreciably bind any plasma proteins (data not shown). In addition, it appears that DAP has a short elimination half-life, because anti-coagulation induced by PRADAXA® returned in 20-30 minutes following an intravenous bolus dose of DAP in rats. Moreover, DAP was stable to sterilization (survived heating to 200° C.) and to storage as a lyophilized powder at 4° C. for more than one year. Summary of anticoagulant reversal by DAP is presented in Table 2.

TABLE 2

Anticoagulant reversal

| Trade Name | Generic Name | Company | Blood Factor Inhibited | Route of Administration | Binds DAP | Reversal Agents |
|---|---|---|---|---|---|---|
| Lovenox ® | Enoxaparin | Sanofi, Sandoz/ | ~80-90% Xa, | s.c. Injection | X | Protamine* & DAP |
| Hibor ® | Bemiparin | Momenta, Rovi | ~10-20% IIa | | | |
| Arixtra ® | Fondaparinux | GSK | Xa | s.c. Injection | X | DAP |
| Eliquis ® | Apixaban | Pfizer, BMS | Xa | Oral | X | DAP |
| Xarelto ® | Rivaroxaban | Bayer, Janssen, J&J | Xa | Oral | X | DAP |
| Argatroban ® | Argatroban | GSK | IIa | s.c. Injection | — | None |
| Pradaxa ® | Dabigatran etexilate | Boehringer Ingelheim | IIa | Oral | X | DAP |

*Protamine partially reverses low molecular weight heparins.

TABLE 3

In vitro in vivo correlation

| Drug Generic Name | DLS Binding Molar Ratio [DAP/drug] | Reversal Molar Ratio [DAP/drug] | in vivo Measure | Blood Factor(s) Inhibited | Route of Administration |
|---|---|---|---|---|---|
| Rivaroxaban | 9 | 3* | Bleeding assay | Xa | Oral |
| Apixaban | 10 | 8* | Bleeding assay | Xa | Oral |
| Fondaparinux | 3 | 130 | Xa kit | Xa | s.c. Injection |
| Bemiparin | 7 | 140 | aPTT | ~80-90% Xa, ~10-20% IIa | s.c. Injection |
| Argatroban | N/A | N/A | aPTT | IIa | s.c. Injection |

*Assumes oral bioavailabilies of 60% for rivaroxaban, 50% for apixaban, and 5% for dabigatran; Assumes 100% bioavailability for injectable anticoagulants.

Summary of in vitro-in vivo correlation of treatment with DAP is presented in Table 3. DLS binding molar ratio is calculated by dividing the lowest mass ratio of DAP to anticoagulant that shows significant binding, defined as an association in phosphate buffered saline above 50 nm in apparent diameter, by the molecular weight ratio of DAP and the anticoagulant. The molecular weights used in the calculations were 512 Da (DAP), 436 Da (rivaroxaban), 460 Da (apixaban), 1.7 kDa (fondaparinux), 3.6 kDa (bemiparin), 628 Da (dabigatran), and 509 Da (ARGATROBAN®). Reversal molar ratio was calculated similarly using the minimal in vivo reversal dose of DAP necessary to achieve reversal as measured by the rat tail transection bleeding assay, chromogenic anti-Xa kit, or by activated partial thromboplastin time (aPTT). For the bleeding assay, the anticoagulant was considered reversed if the blood loss over a period of 30 minutes after tail transection, with the cut tail immersed in room temperature saline, was within 25% of the control (no anticoagulant administered). As measured by the Xa kit, reversal was achieved when the effective anticoagulant concentration was brought below the minimum effective concentration (MEC) for anticoagulation. As measured by aPTT, reversal was considered achieved when an anticoagulated rat aPTT returned to within 10% of baseline. In the case of fondaparinux, although 200 mg/kg DAP was the lowest dose administered in vivo, the in vitro data indicate that significantly lower reversal doses are possible.

The entire contents of all references, patent applications, and patents cited throughout this application are hereby incorporated by reference herein.

EXAMPLES

The invention will be further illustrated in the following nonlimiting Examples. These Examples are set forth to aid in the understanding of the invention but are not intended to, and should not be construed to, limit its scope in any way. The Examples do not include detailed descriptions of conventional methods that are well known to those of ordinary skill in the art.

Example 1

In Vitro Stability Testing of Diarginine Piperazine ("DAP")

Materials and Methods

An acetate salt of DAP was prepared as described herein. As described in these examples, DAP solid or powder refers to the acetate salt, while DAP in solution refers to the free base as the salt ionizes in aqueous solution. As described in these examples, the DAP compound used was the compound of Formula VII.

The DAP powder was tested for thermal stability in two ways. DAP was stored at 4° C. for 7 months prior to use. Additionally, the DAP solid was tested by differential scanning calorimetry (DSC) by heating from −20° C. to 200° C., back to −20° C. and again to 200° C.

Results

DAP powder was stable at 4° C. for more than 12 months. The results of DSC are shown in FIG. 1. The second heat ("2") showed similar thermal behavior to the first heat ("1"), indicating that DAP survived repeated heating to 200° C. This finding indicates that DAP is able to survive heating to temperatures above those necessary for sterilization.

Example 2

Binding of DAP to Heparin and LMWH

Materials and Methods

Dynamic light scattering (DLS) was used to assess association of 1 mg/ml unfractionated heparin and 1 mg/ml bemiparin (LMWH; HIBOR®), either alone or in combination with 100 mg/ml DAP in water (mass ratios of 100:1 of DAP to heparin or LMWH).

Results

Figure 2:
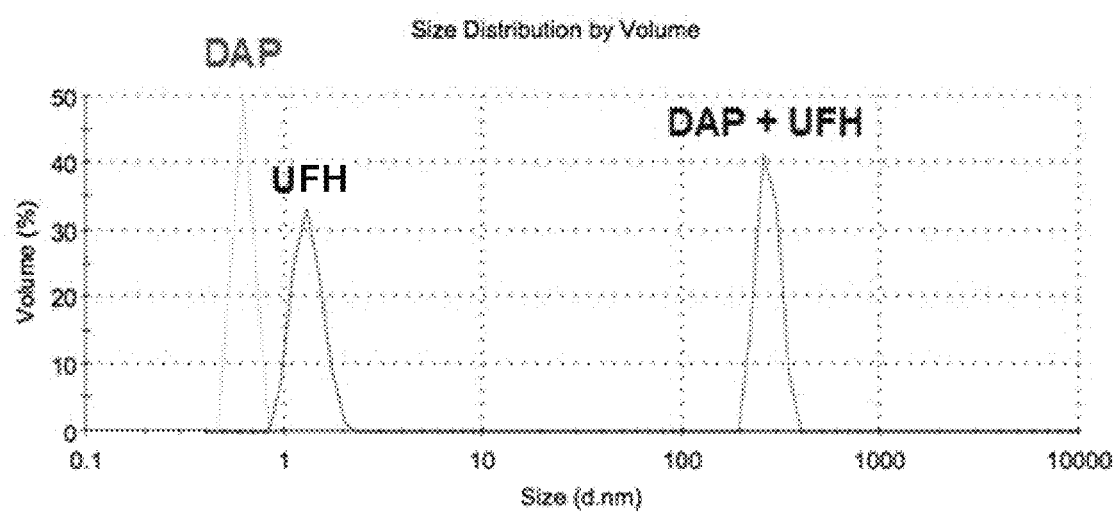
FIG. 2 is a graph of DAP alone, UFH alone, and DAP-UFH combination, as a function of volume percent compared to size (d·nm) as measured by Dynamic Light Scattering (DLS).

DAP physically associated in water with both unfractionated heparin (FIG. 2) and LMWH (not shown) to form physical associations that increase the apparent diameter. When solutions of DAP were mixed with solutions of LMWH or unfractionated heparin, they formed particles due to their physical interactions, which supports the theory that DAP could reverse heparin and LMWH anticoagulation by physically associating with these molecules.

Example 3

DAP Binding to Anticoagulants as Measured by DLS

Materials and Methods

Rivaroxaban (XARELTO®) alone, DAP alone, and DAP:rivaroxaban combinations at mass ratios of 1:1 and 10:1 were added into an aqueous solution and analyzed by dynamic light scattering (DLS) to assess association of the DAP and rivaroxaban. A similar experiment was conducted on apixaban (ELIQUIS®) alone, DAP alone, and DAP:apixaban combinations at mass ratios of 1:1, 10:1 and 100:1. Fondaparinux (ARIXTRA®) alone, DAP alone, and fondaparinux:DAP combinations at mass ratios of 1:1, 10:1 and 100:1 were similarly tested. LMWH (bemiparin; HIBOR®), alone, DAP alone, and LMWH:DAP combinations at mass ratios of 1:1, 10:1, and 100:1 were also tested. The concentration of LMWH tested was 0.1 mg/ml. Therefore, at 1:1, 0.1 mg/ml DAP was tested, at 10:1, 1 mg/ml was tested, and at 100:1, 10 mg/ml DAP was tested.

Additionally, dabigatran alone, DAP alone, and dabigatran:DAP combination at mass ratios of 1:1, 10:1, 100:1, 1,000:1, and 10,000:1 DAP were tested. Finally, ARGATROBAN® alone, DAP alone, or combinations of argatroban:DAP at mass ratios of 1:1, 10:1, 100:1, and 1,000:1 were tested.

Results

Figure 3:
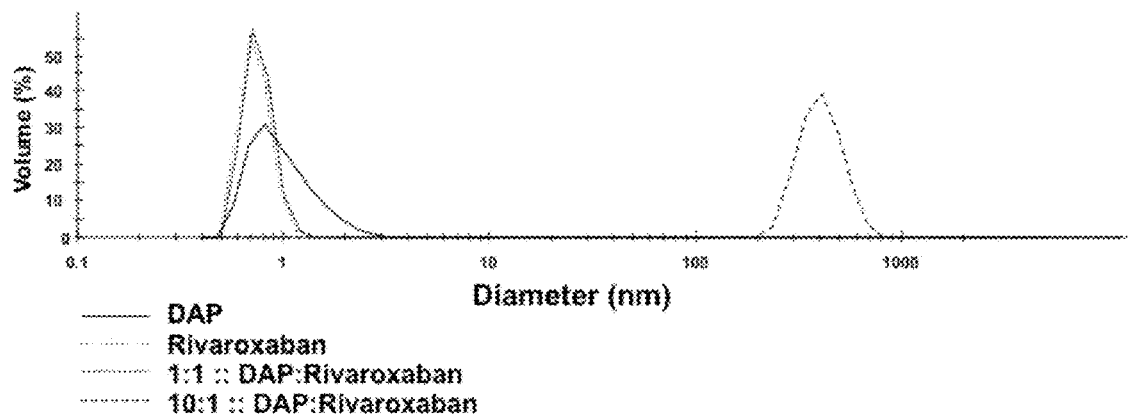
FIG. 3 is a graph of DAP alone, rivaroxaban alone and DAP-rivaroxaban in ratios of 1:1 and 10:1, DAP:rivaroxaban, as a function of volume (percent) compared to size (d·nm) as measured by DLS.
Figure 4:
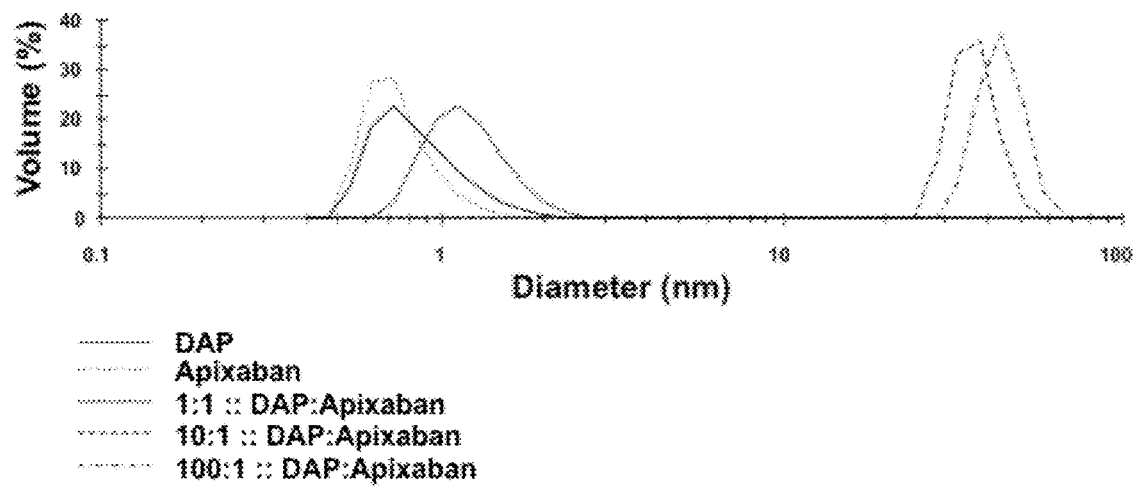
FIG. 4 is a graph of DAP alone, apixaban alone and DAP-apixaban binding in ratios of 1:1, 10:1 and 100:1, as a function of volume (percent) compared to size (d·nm) as measured by DLS.
Figure 5:
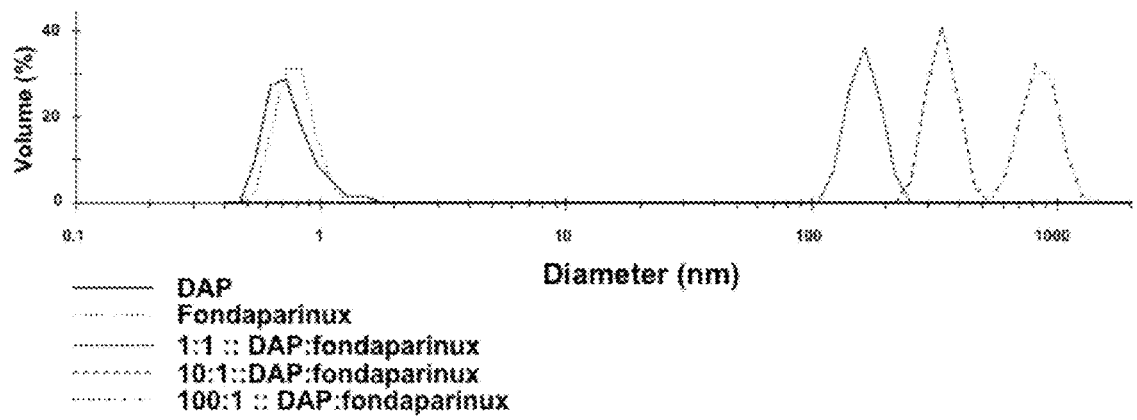
FIG. 5 is a graph of DAP alone, fondaparinux alone and DAP-fondaparinux binding in ratios of 1:1, 10:1 and 100:1, as a function of volume (percent) compared to size (d·nm) as measured by DLS.
Figure 6:
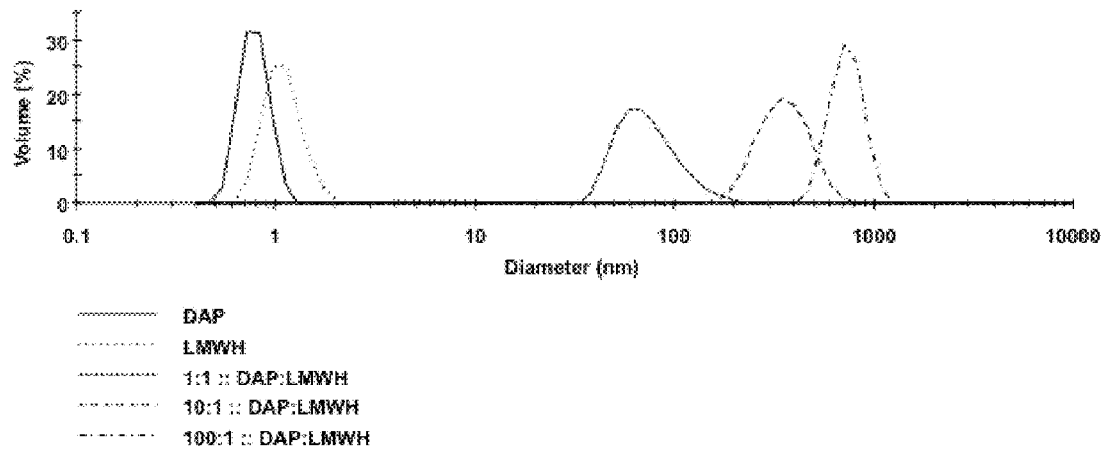
FIG. 6 is a graph of DAP alone, LMWH alone and DAP-LMWH binding in ratios of 1:1, 1:10 and 100:1, as a function of volume (percent) compared to size (d·nm) as measured by DLS.
Figure 7:
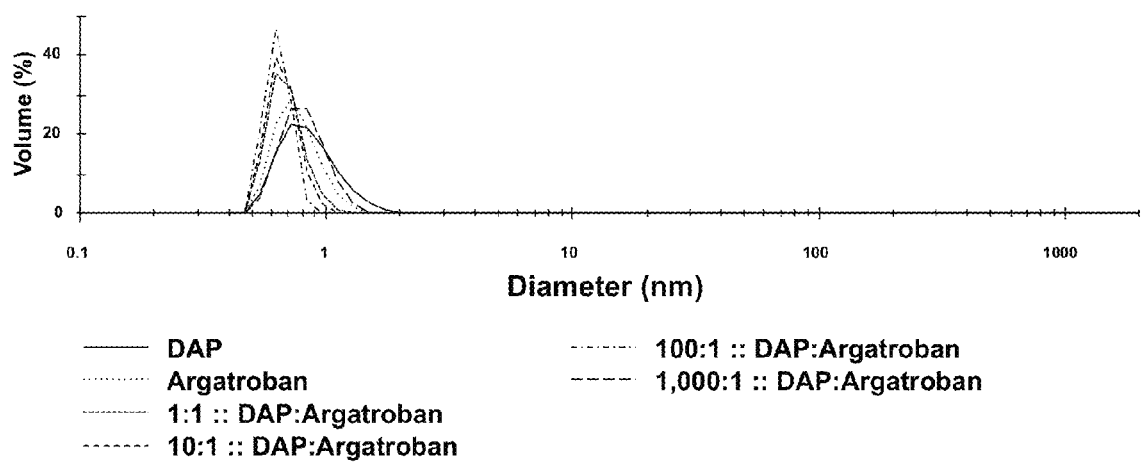
FIG. 7 is a graph of DAP alone, argatroban alone and DAP-argatroban binding in ratios of 1:1, 10:1, 100:1, and 1000:1, as a function of volume (percent) compared to size (d·nm) as measured by DLS.

The results are shown in FIG. 3 for rivaroxaban; FIG. 4 for apixaban;

FIG. 5 for fondaparinux (ARIXTRA®), FIG. 6 for LMWH; and FIG. 7 for argatroban. Each figure shows individual peaks representing DAP and the anticoagulant alone in aqueous solution. When the anticoagulant was mixed with DAP at sufficiently high mass ratios, a change in size was observed. In this assay, even a slight increase in size indicates physical interaction between the two; however, only significant shifts in the apparent diameter are used in assessing the in vitro in vivo correlation. Apparent diameter is a measure of the degree of interaction.

Example 4

DAP Reversal of LMWH Anticoagulation In Vivo

Materials and Methods

A male albino rat, weighing 470 g, was administered 10 mg of bemiparin (an overdose of LMWH) by subcutaneous injection. aPTT time was measured over the course of five hours. Four hours after LMWH administration, the rat received an intravenous dose of 200 mg/kg of DAP (100 mg DAP).

Figure 8:
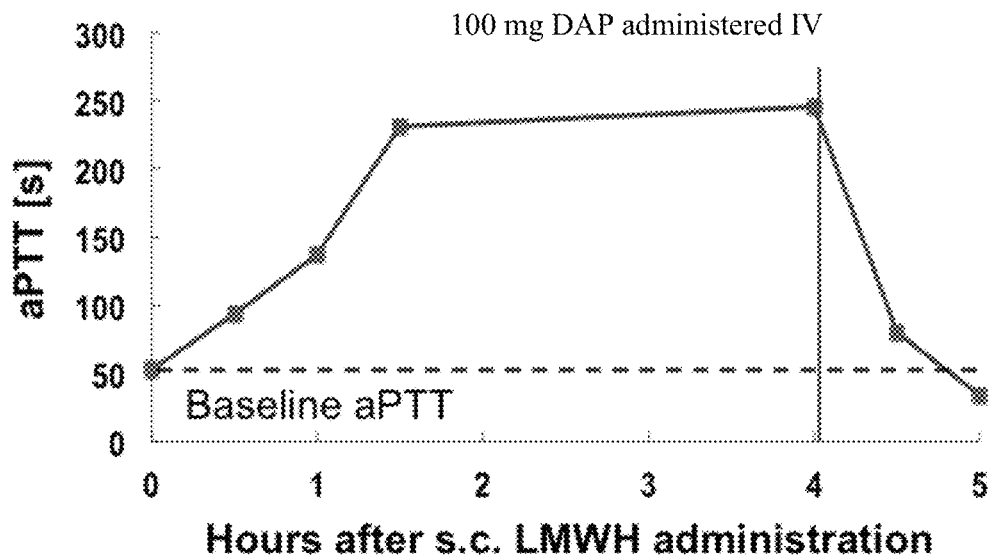
FIG. 8 is a graph of activated partial thromboplastin time (aPTT, seconds) measured over time (hours) during five hours after subcutaneous administration of 10 mg of bemiparin (LMWH) to a rat. Four hours into treatment, the rat received an intravenous dose of 200 mg/kg (100 mg) DAP.

Results
Upon administration of LMWH, the aPTT rose from 53 to 246 seconds over the course of four hours. Intravenous administration of 200 mg/kg of DAP (100 mg DAP) brought aPTT time below baseline within 60 minutes (FIG. 8).

Example 5

Figure 9:
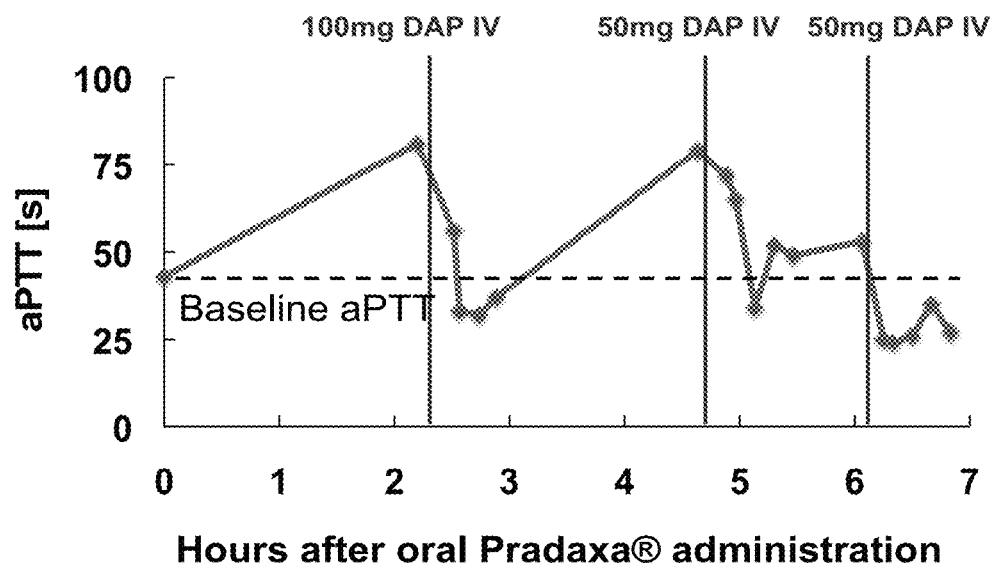
FIG. 9 is a graph of activated partial thromboplastin time (aPTT, seconds) measured over time (hours) after oral administration of PRADAXA® (dabigatran) to a rat followed by intravenous administration of 200 and 100 mg/kg (100 mg and 50 mg) DAP.
Figure 13:
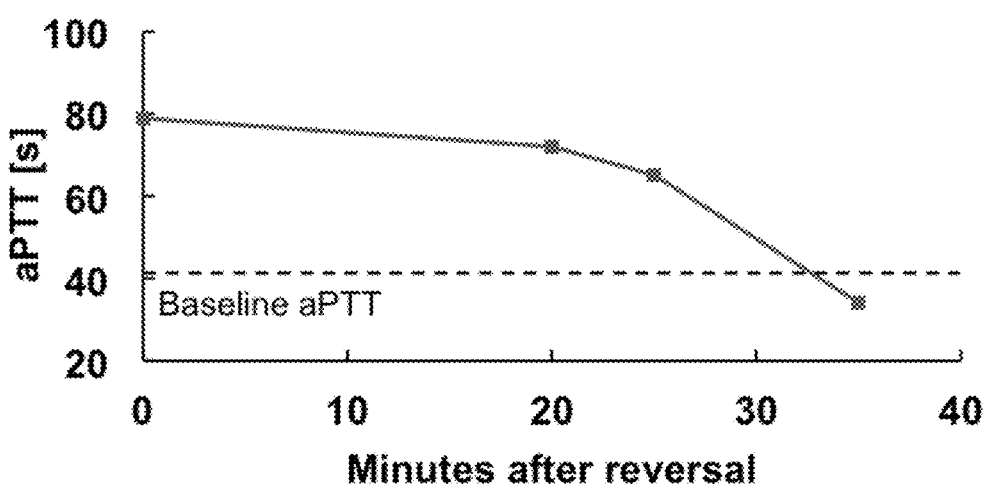
FIG. 13 is a graph of aPTT (seconds) measured over time (minutes after reversal) after oral administration of 15.5 mg/kg PRADAXA® (dabigatran) to a rat, followed by intravenous administration of 100 mg/kg DAP (i.e., "reversal").
Figure 14:
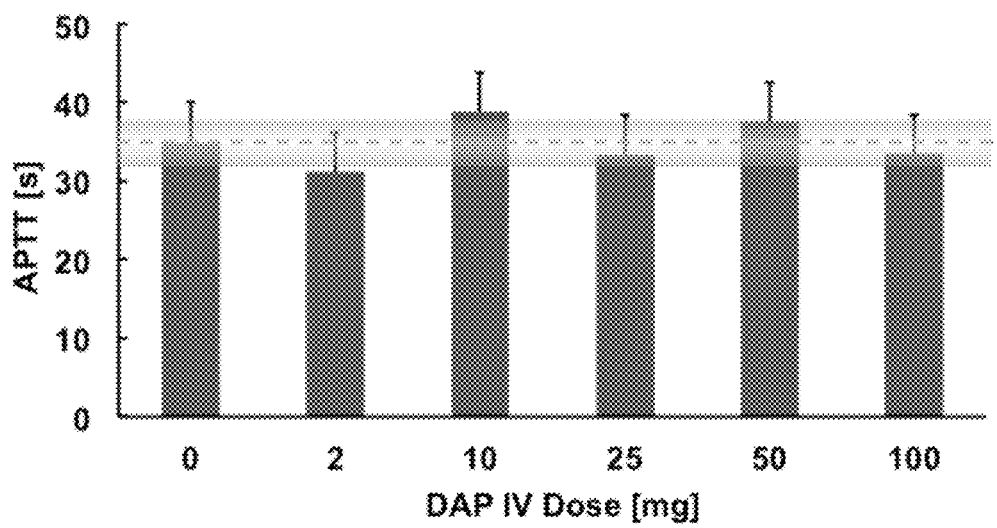
FIG. 14 is a graph of the aPTT time (seconds) for 0, 2, 10, 25, 50, and 100 mg intravenously administered DAP.

DAP Reversal of Dabigatran (PRADAXA®) Anticoagulation In Vivo; an Overdose Study Materials and Methods
A male albino rat, weighing 430 g, was administered 40 mg/kg of PRADAXA® (20 mg PRADAXA®; overdose of PRADAXA®) by oral gavage.
Approximately 2 hours into PRADAXA® treatment, 200 mg/kg DAP (100 mg DAP) was administered as an intravenous bolus injection. Approximately 2 hours later, the rat was administered a dose of 100 mg/kg of DAP (50 mg DAP). In another hour, the rat was administered another dose of 100 mg/kg of DAP (50 mg DAP). aPTT was measured throughout the course of the entire treatment.
Results
The results are shown in FIGS. 9 and 13. 2 hours following administration of PRADAXA®, aPTT rose from 43 to 81 seconds, showing significant anti-coagulation. 100 mg of DAP was administered as an intravenous bolus injection, which brought aPTT down below baseline within 25 minutes. 2 hours later, aPTT had risen back to 79 seconds and the rat was administered a dose of 50 mg of DAP. Within 30 minutes, aPTT was brought down below baseline. Both times, within 60 minutes following DAP administration, the aPTT levels had returned above baseline. After the second dose of DAP, the aPTT rose to 53 seconds. A third dose of DAP, 100 mg/kg of DAP (50 mg DAP), was administered intravenously and the aPTT was dropped to baseline within 20 minutes. FIG. 13 demonstrates a similar experiment where, after 15.5 mg/kg administration of PRADAXA®, the aPTT returned to normal within about 30 minutes of initiation of 100 mg/kg DAP treatment.

Example 6

DAP Reversal of Unfractionated Heparin ("UHF") Anticoagulation In Vivo

Figure 10:
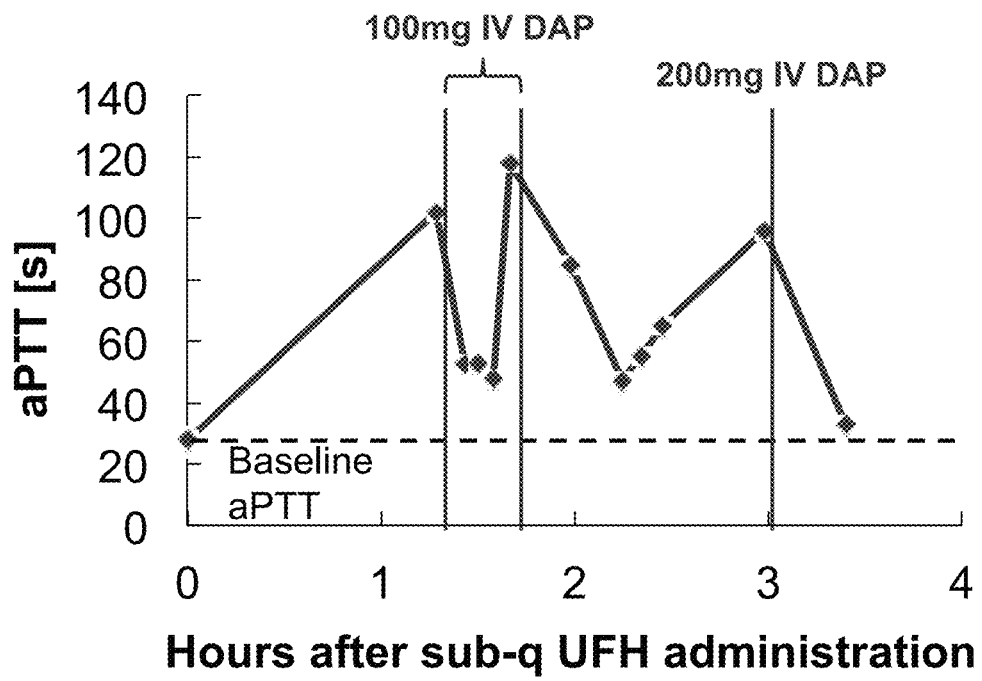
FIG. 10 is a graph of activated partial thromboplastin time (aPTT) measured over time (hours) after subcutaneous administration of unfractionated heparin (UFH) to a rat followed by intravenous administration of 200 mg/kg (100 mg) and 400 mg/kg (200 mg) DAP.

Materials and Methods
A male albino rat, weighing 515 g, was administered 10 mg/kg of unfractionated heparin (5 mg UFH) by subcutaneous injection.
200 mg/kg of DAP (100 mg DAP) was administered as two intravenous bolus injections after UFH administration. Subsequently, the rat was administered a dose of 400 mg/kg of DAP (200 mg of DAP). aPTT was measured throughout the course of the entire treatment.
Results
As demonstrated in FIG. 10, the aPTT time rose significantly from 28 to 102 seconds over the course of one hour after administration of heparin. 100 mg of DAP was administered intravenously and it brought aPTT time to 48 seconds in 20 minutes. Within 1 hour, aPTT rose to 120 seconds, then another 100 mg of DAP was administered intravenously. In 15 minutes, the aPTT was lowered to 47 seconds. Within 1 hour, aPTT rose to 96 seconds, then a dose of 200 mg of DAP was administered intravenously. 10 minutes after, aPTT dropped to 33 seconds.

Example 7

DAP Reversal of Rivaroxaban (XARELTO®) Anticoagulation In Vivo

Figure 11:
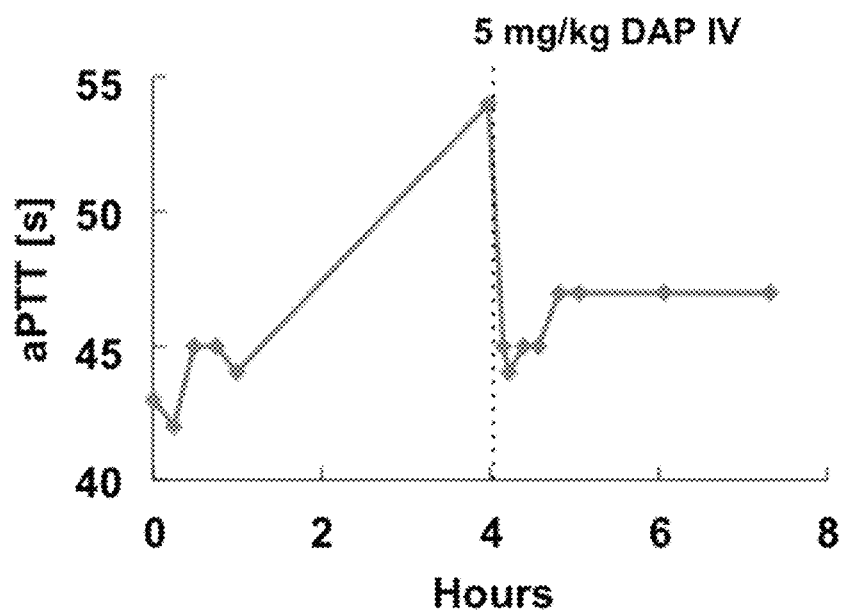
FIG. 11 is a graph of aPTT (seconds) measured over time (hours) after oral administration of 5 mg/kg of rivaroxaban to a rat followed by intravenous administration of 5 mg/kg (2 mg) DAP.

Materials and Methods
5 mg/kg rivaroxaban (XARELTO®) was orally administered to rats. After four hours, 5 mg/kg of DAP (2 mg DAP) was administered intravenously. aPTT were measured at zero, 15, 30, 45, 60 and 240 minutes, prior to administration of DAP. aPTT was again measured at about 5, 10, 25, 35, 45, 60, 120, and 240 minutes after DAP administration.
Results
The results are shown in FIG. 11. DAP effectively reversed the rivaroxaban (XARELTO®) anticoagulation in vivo in rats.

Example 8

DAP Reversal of Fondaparinux (ARIXTRA®) Anticoagulation In Vivo

Figure 12:
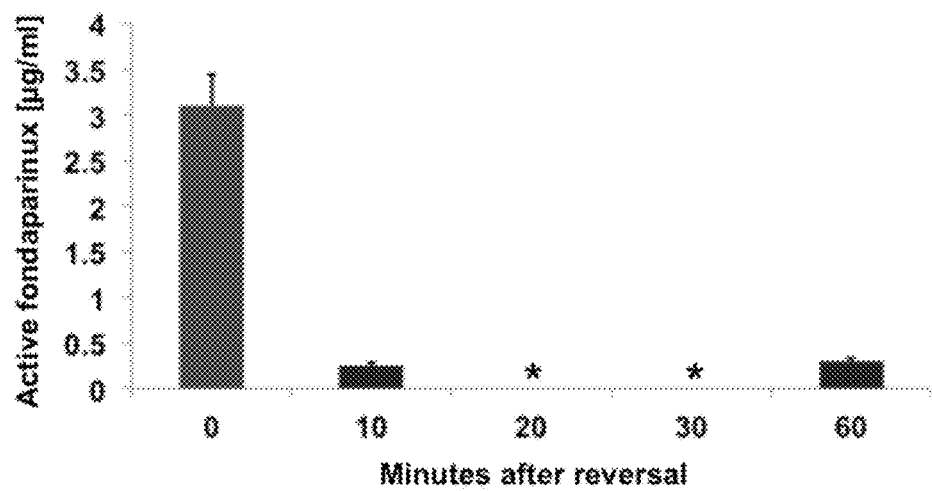
FIG. 12 is a graph of active fondaparinux concentration (µg/mL) measured over time (minutes after reversal) after a subcutaneous administration of 5 mg/kg fondaparinux to a rat, followed by intravenous administration of 200 mg/kg DAP (i.e., "reversal").

Materials and Methods
5 mg/kg fondaparinux was administered subcutaneously to rats. 200 mg/kg DAP was administered intravenously after 2 hours. Activity was measured by chromogenic 510 k cleared Factor Xa Assay (Biophen) at 10, 20, 30 and 60 minutes after DAP adminsitration.
Results
FIG. 12 demonstrates DAP-mediated reversal of fondaparinux anticoagulation within 10 minutes of administration.

Example 9

Intravenous DAP does not Influence aPTT

Materials and Methods
0, 2, 10, 25, 50 or 100 mg DAP were administered intravenously to male, weight matched CD rats and aPTT was measured.
Results
The results shown in FIG. 16 demonstrate that DAP administered intravenously did not influence aPTT in a dose dependent fashion in the absence of anticoagulants. Error bars represent standard error from seven aPTT measurements averaged over 90 minutes.

Example 10

DAP Reversal of Anticoagulation in a Rat Tail Transection Model

Materials and Methods
Three rats each were administered 2 mg of rivaroxaban. One rat received a sham reversal containing no DAP, the second received 2.5 mg of DAP, and the third received 12.5 mg DAP. A fourth fat received sham anticoagulant and reversal doses ("sham"). 20 minutes after the reversal dose, tails were transected 1 mm from the tip, placed in room temperature saline, and blood loss was collected for 30 minutes and then weighed.
Same procedures were used with 1.25 mg apixaban (ELIQUIS®) alone or in combination with 5 or 12.5 mg DAP; with 15.5 mg dabigatran etexilate (PRADAXA®) alone or in combination with 5 or 12.5 mg DAP; and with 5 mg edoxaban (LIXIANA®) alone or in combination with 12.5 mg DAP.

Results

Figure 15:
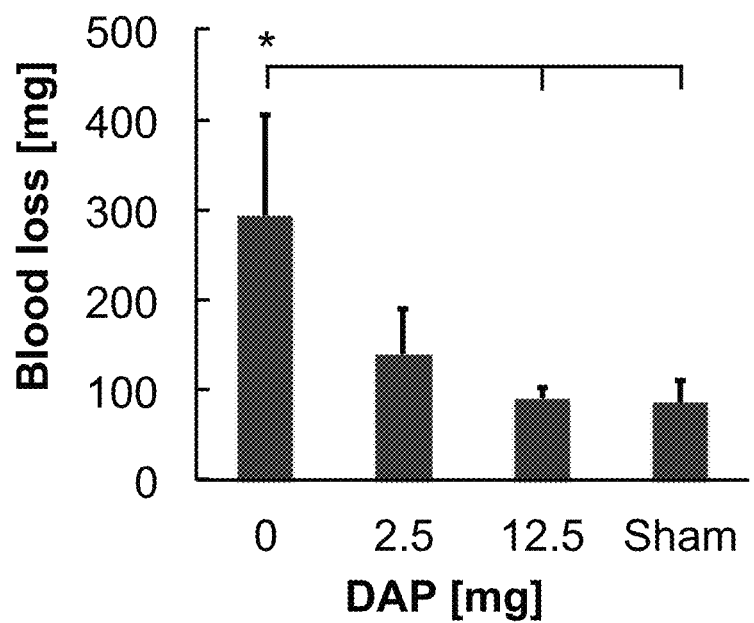
FIG. 15 is a graph of blood collected (i.e., cumulative blood loss) over 30 minutes in a rat tail transection bleeding assay in rats receiving 2 mg rivaroxaban and 0 mg DAP, 2 mg rivaroxaban and 2.5 mg DAP, 2 mg rivaroxaban and 12.5 mg DAP, or sham reversal and anticoagulant doses ("sham"). With groups of three age-matched rats, 12.5 mg of DAP reduced blood loss to sham dose levels yielding a statistically significant difference (* $p<0.05$) from rats receiving rivaroxaban only.
Figure 16:
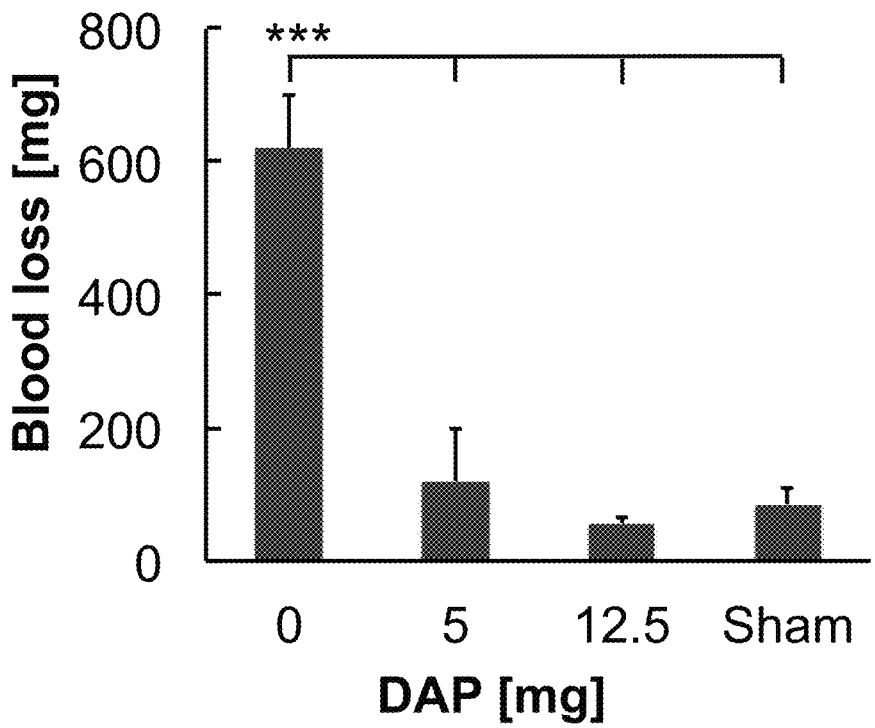
FIG. 16 is a graph of blood collected (i.e., cumulative blood loss) over 30 minutes in a rat tail transection bleeding assay in rats receiving 1.25 mg apixaban and 0 mg DAP, 1.25 mg apixaban and 5 mg DAP, 1.25 mg apixaban and 12.5 mg DAP, or sham reversal and anticoagulant doses ("sham"). With groups of three age-matched rats, 5 mg and 12.5 mg of DAP reduced blood loss to sham dose levels yielding a statistically significant difference (*** $p<0.01$) from rats receiving apixaban only.
Figure 17:
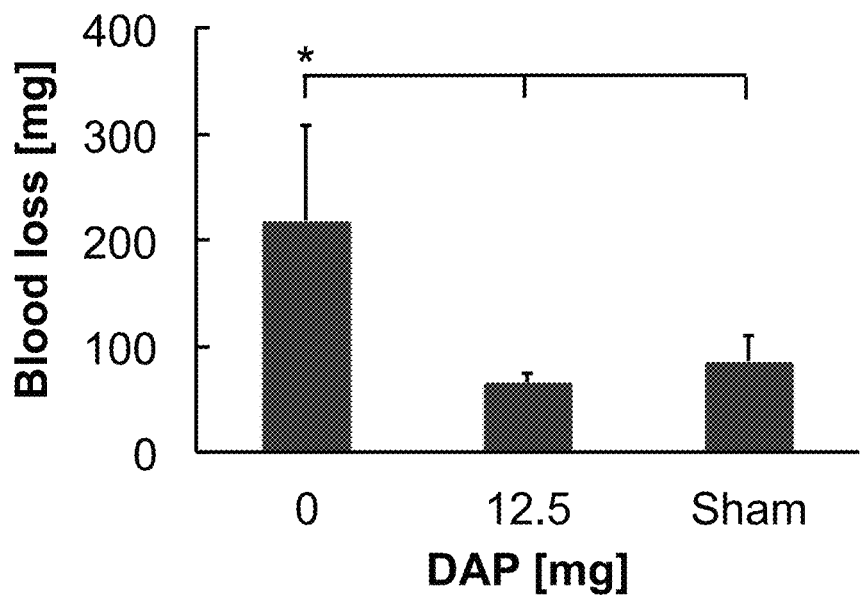
FIG. 17 is a graph of blood collected (i.e., cumulative blood loss) over 30 minutes in a rat tail transection bleeding assay in rats receiving 1.25 mg edoxaban and 0 mg DAP, 1.25 mg edoxaban and 12.5 mg DAP, or sham reversal and anticoagulant doses ("sham"). With groups of three age-matched rats, 12.5 mg of DAP reduced blood loss to sham dose levels yielding a statistically significant difference (* $p<0.05$) from rats receiving edoxaban only.
Figure 18:
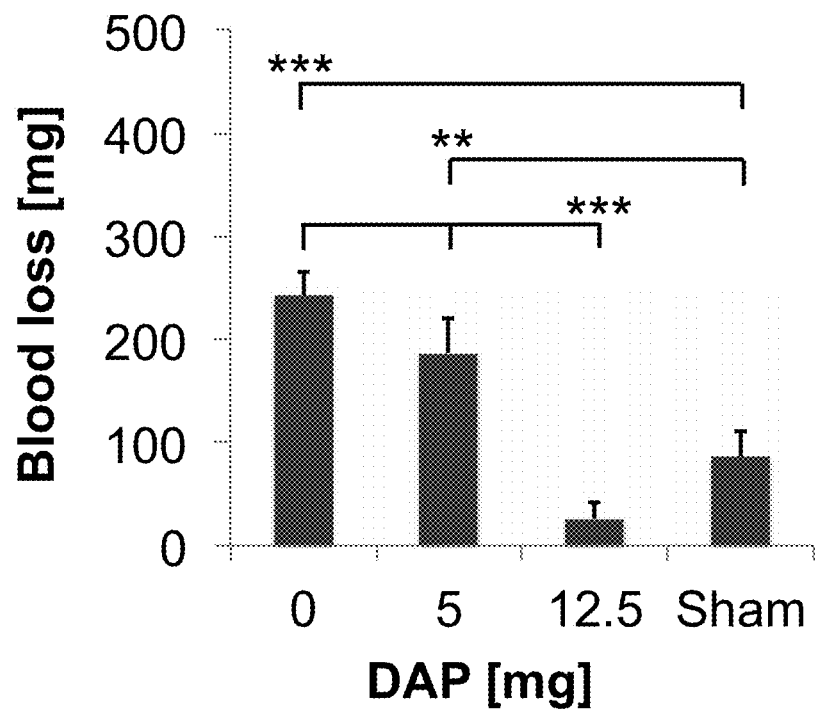
FIG. 18 is a graph of blood collected (i.e., cumulative blood loss) over 30 minutes in a rat tail transection bleeding assay in rats receiving 15 mg dabigatran etexilate and 0 mg DAP, 15 mg dabigatran etexilate and 5 mg DAP, 15 mg dabigatran etexilate and 12.5 mg DAP, or sham reversal and anticoagulant doses ("sham"). With groups of three age-matched rats, 12.5 mg of DAP reduced blood loss to sham dose levels yielding a statistically significant difference (*** $p<0.01$) from rats receiving dabigatran etexilate only.

The results are shown in FIG. 15 for rivaroxaban, in FIG. 16 for apixaban, in FIG. 17 for edoxaban, and in FIG. 18 for dabigatran etexilate. The rat tail transection bleeding assay is analogous to the clinical situation in which acute anticoagulant reversal is needed. Results show that DAP effectively reversed anticoagulant activity leading to statistically significant reduction in blood loss compared to rats receiving anticoagulant only.

Example 11

DAP Reversal of Rivaroxaban (XARELTO®) Anticoagulation in Freshly Drawn Human Blood Ex Vivo Materials and Methods Human blood was drawn from a volunteer. Rivaroxaban at 0.25 µg/ml was added alone or in combination with 50 µg/ml DAP. Controls contained 50 µg/ml DAP or saline. aPTT was measured within 2 minutes of blood collection.

Results

Figure 19:
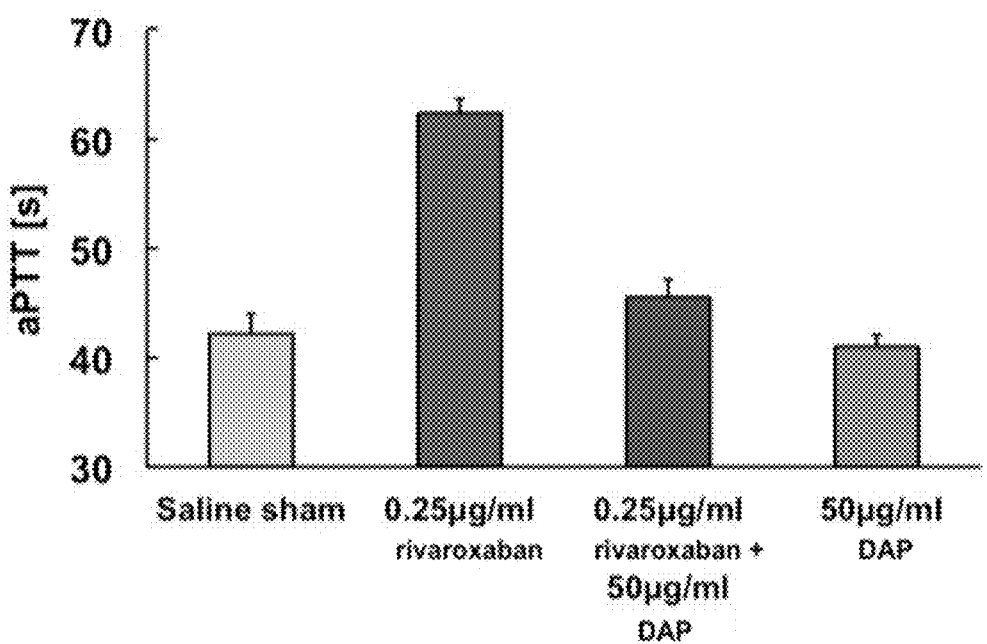
FIG. 19 is a graph of aPTT (seconds) measured in freshly drawn human blood treated ex vivo with 50 micrograms/ml DAP, 0.25 micrograms/ml rivaroxaban, 50 micrograms/ml DAP and 0.25 micrograms/ml rivaroxaban, or saline.

FIG. 19 demonstrates that administration of DAP led to a reversal of rivaroxaban-induced anticoagulation in freshly drawn human blood, as measured by aPTT. Error bars represent standard error from three independent experiments.

Example 12

DAP Reversal of Rivaroxaban and Apixaban Anticoagulation in Human Plasma Ex Vivo Materials and Methods 218 µg/L or 459 µg/L of rivaroxaban was added to human plasma, with or without 1,250 µg/L or 6,250 µg/L of DAP, respectively. Similarly, 156 µg/L or 313 µg/L of apixaban was added to human plasma with or without 1,156 µg/L or 3,125 µg/L of DAP, respectively. DAP effect on anticoagulation was measured by 510 k cleared Biophen anti-Factor Xa chromogenic assay. Rivaroxaban concentrations were determined by comparison with plasma calibration standards, while apixaban concentrations were inferred from stock solution dilutions as calibration standards are not yet available.

Results

Figure 20:
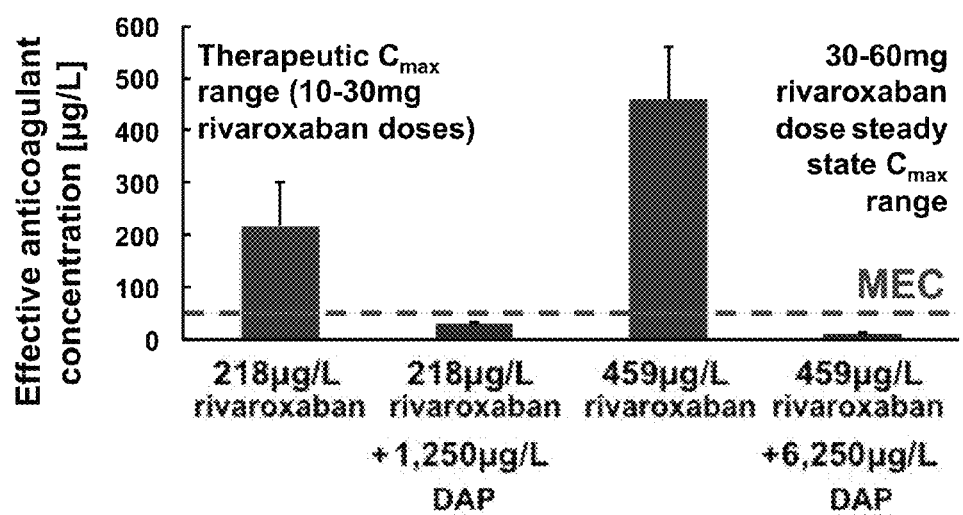
FIG. 20 is a graph showing effective anticoagulant concentration measured by anti-factor Xa activity assay in human plasma treated ex vivo with of 218 µg/L rivaroxaban alone or in combination with 1,250 mg/L DAP, and 459 µg/L rivaroxaban alone or in combination with 6,250 µg/L DAP.
Figure 21:
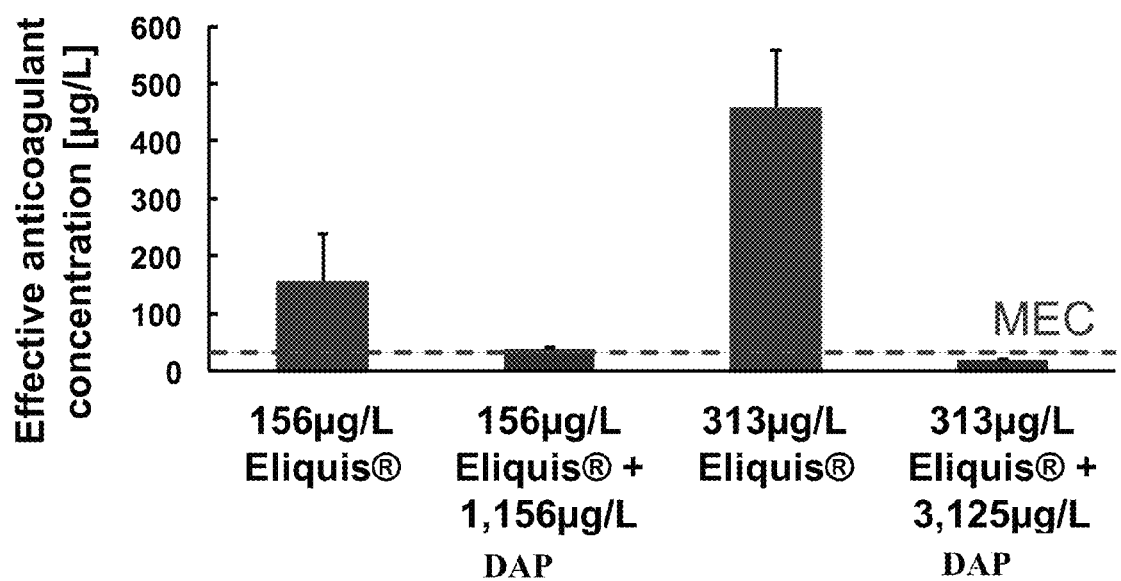
FIG. 21 is a graph showing effective anticoagulant concentration measured by anti-factor Xa activity assay in human plasma treated ex vivo with 156 μg/L apixaban alone or in combination with 1,156 μg/L DAP, and 313 μg/L apixaban alone or in combination with 3,125 μg/L DAP.

For both concentrations of rivaroxaban and apixaban, DAP returned the effective anticoagulant concentration to below the minimum effective concentration. FIG. 20 shows the results for rivaroxaban and FIG. 21 shows the results for apixaban.

Example 13

DAP Dose-Dependent Reversal of Rivaroxaban Anticoagulation in Human Plasma Ex Vivo Materials and Methods 218 µg/L rivaroxaban was added to human plasma either alone or in combination with 1.25, 12.5, 125, or 1,250 µg/L of DAP. Factor Xa activity was measured by 510 k cleared Biophen anti-Xa chromogenic assay kit. Rivaroxaban concentrations were determined by comparison with plasma calibration standards.

Results

Figure 22:
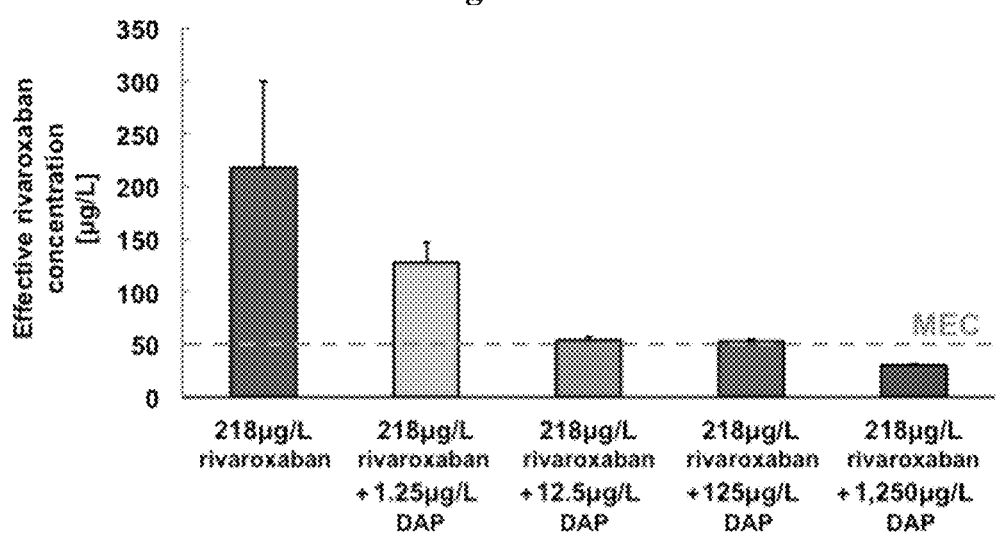
FIG. 22 is a graph showing effective anticoagulant concentration measured by anti-factor Xa activity assay in human plasma treated ex vivo with 218 μg/L rivaroxaban, alone or in combination with increasing amounts (1.25, 12.5, 125, and 1,250 μg/L) of DAP.

FIG. 22 demonstrates that DAP was effective in dose-dependent reversal of rivaroxaban anticoagulation in human plasma, as demonstrated by its effect on rivaroxaban concentration (measured by Factor Xa activity assay).

What is claimed is:

1. A compound represented by formula II:

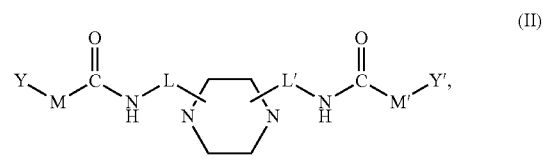

(II)

or a pharmaceutically acceptable salt thereof, wherein:
L and L' are each a substituted or unsubstituted $C_1$ to $C_{10}$ alkylene chain;
M and M' are each a substituted $C_1$ to $C_{10}$ alkylene chain; and
Y and Y' are each

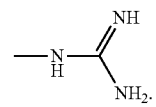

2. The compound of claim 1, wherein L and/or L' is a substituted or unsubstituted alkylene chain that is $C_1$ to $C_6$.

3. The compound of claim 1, wherein the compound is represented by formula III:

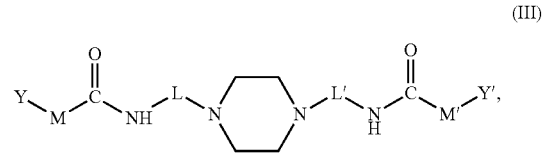

(III)

or a pharmaceutically acceptable salt thereof.

4. The compound of claim 3, wherein the compound is represented by formula IV:

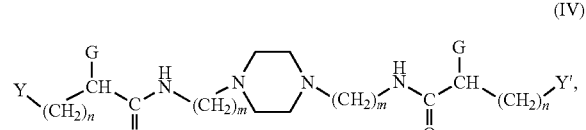

(IV)

or a pharmaceutically acceptable salt thereof,
wherein n is 3 to 5, m is 3 to 6 and G is selected from —$NH_2$ and OH.

5. The compound of claim 4, wherein G is amino.

6. A compound of formula V

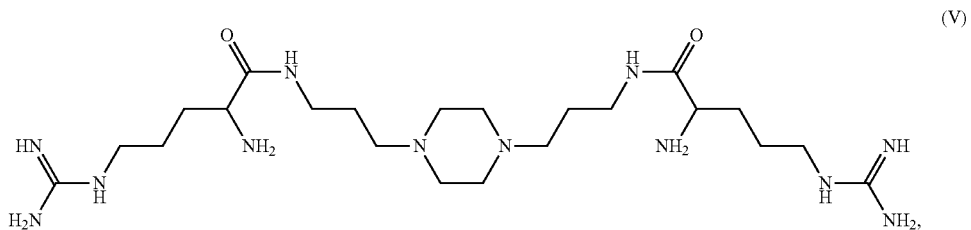 [SMILES: N=C(N)NCCCC(N)C(=O)NCCCN1CCN(CCCNC(=O)C(N)CCCNC(=N)N)CC1]

or a pharmaceutically acceptable salt thereof.

7. A compound of formula VI

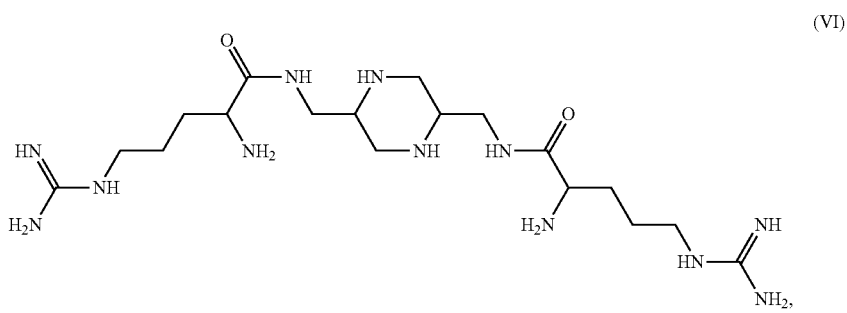 [SMILES: N=C(N)NCCCC(N)C(=O)NCC1CNC(CNC(=O)C(N)CCCNC(=N)N)CN1]

or a pharmaceutically acceptable salt thereof.

8. A compound of formula VII

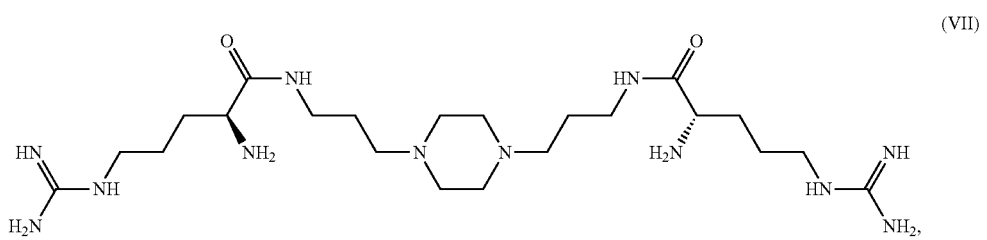 [SMILES: N=C(N)NCCC[C@H](N)C(=O)NCCCN1CCN(CCCNC(=O)[C@@H](N)CCCNC(=N)N)CC1]

or a pharmaceutically acceptable salt thereof.

9. A compound of formula VIII

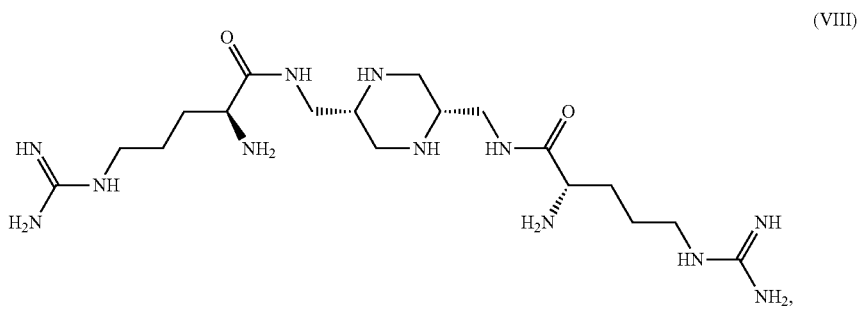 [SMILES: N=C(N)NCCC[C@H](N)C(=O)NC[C@H]1CN[C@@H](CNC(=O)[C@@H](N)CCCNC(=N)N)CN1]

or a pharmaceutically acceptable salt thereof.

10. A pharmaceutical composition comprising the compound of any one of claims 2-5 and 6-9 and a pharmaceutically acceptable carrier.

11. The pharmaceutical composition of claim 10, wherein the composition is adapted for enteral administration.

12. The pharmaceutical composition of claim 11, wherein the composition is adapted for oral administration.

13. The pharmaceutical composition of claim 10, wherein the composition is adapted for parenteral administration.

14. The pharmaceutical composition of claim 13, wherein the composition is adapted for intravenous or subcutaneous administration.

15. The pharmaceutical composition of claim 12, wherein the composition is a daily dosage that comprises the compound in an amount of about 0.01 mg/kg to about 100 mg/kg of body weight of a patient.

16. The pharmaceutical composition of claim 15, wherein the daily dosage composition comprises the compound in an amount of about 0.01 mg/kg to about 25 mg/kg of body weight of the patient.

17. The pharmaceutical composition of claim 12, wherein the composition is in the form of a capsule or tablet.

18. The pharmaceutical composition of claim 12, wherein the composition is an aqueous solution.

* * * * *

UNITED STATES PATENT AND TRADEMARK OFFICE
CERTIFICATE OF CORRECTION

PATENT NO. : 9,522,892 B2
APPLICATION NO. : 13/688442
DATED : December 20, 2016
INVENTOR(S) : Solomon S. Steiner et al.

Page 1 of 2

It is certified that error appears in the above-identified patent and that said Letters Patent is hereby corrected as shown below:

On the Title Page

[56] REFERENCES CITED:
Foreign Patent Documents, "WO WO03082809 A1* 10/2003" should read --WO 03/082809 A1* 10/2003--.

In the Specification

Column 2:
Line 63, "has been" should read --have been--.

Column 4:
Line 16, "or pharma-" should read --or a pharma- --; and
Line 30, "Yet" should read --In yet--.

Column 8:
Line 63, "with of" should read --with--.

Column 10:
Line 10, "chains" should read --chain--; and
Line 43, "bihetereo-" should read --bihetero- --.

Column 12:
Line 43, "Yet" should read --In yet--.

Column 20:
Line 62, "powder" should read --powdered--.

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*

Column 21:
Line 56, "beads" should read --beads,--; and
Line 57, "amount" should read --amounts--.

Column 24:
Line 41, "D-glucanopyranos yl-(1→4)-O-β-D-glucopyra-nuronosyl-" should read
--D-glucanopyranosyl-(1→4)-O-β-D-glucopyranuronosyl- --.

Column 26:
Line 39, "maybe" should read --may be--.

Column 29:
Line 6, "herein above." should read --hereinabove--.

Column 30:
Table 3,
"Argatroban    N/A    N/A    aPTT    IIa    s.c. Injection" should read
--Argatroban    N/A    N/A    aPTT    IIa    s.c. Injection
    Assumes oral bioavailabilities of 60% for rivaroxaban, 50% for
    apixaban, and 5% for dabigatran; Assumes 100% bioavailability
    for injectable anticoagulants.-- and
Lines 58-60, "Assumes oral bioavailabilities of 60% for rivaroxaban, 50% for apixaban,
    and 5% for dabigatran; Assumes 100% bioavailability for injectable
    anticoagulants." should be deleted.

Column 32:
Lines 45-46, "for apixaban;
    FIG. 5 for fondaparinux (ARIXTRA®), FIG. 6 for" should read
--for apixaban; FIG. 5 for fondaparinux (ARIXTRA®); FIG. 6 for--.

Column 34:
Line 9, "aPTT were" should read --aPTT was--;
Line 28, "adminsitration." should read --administration.--; and
Line 54, "fat" should read --rat--.

In the Claims

Column 37:
Line 66, "claims 2-5 and 6-9" should read --claims 1-9--.